(12) United States Patent
Gil et al.

(10) Patent No.: US 7,985,230 B2
(45) Date of Patent: Jul. 26, 2011

(54) SYSTEM AND METHOD OF HARVESTING OSTEOCHONDRAL PLUGS

(75) Inventors: Carlos E. Gil, Collierville, TN (US); Daniel A. Shimko, Germantown, TN (US); Jeetendra Bharadwaj, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 300 days.

(21) Appl. No.: 11/494,380

(22) Filed: Jul. 27, 2006

(65) Prior Publication Data

US 2008/0027447 A1    Jan. 31, 2008

(51) Int. Cl.
A61B 17/58 (2006.01)
A61B 17/60 (2006.01)
A61F 2/00 (2006.01)

(52) U.S. Cl. .......................................... 606/96
(58) Field of Classification Search ............... 606/95–98, 606/80–89, 79
See application file for complete search history.

(56) References Cited

U.S. PATENT DOCUMENTS

| | | | | |
|---|---|---|---|---|
| 4,613,324 A | * | 9/1986 | Ghajar | 604/539 |
| 4,641,651 A | | 2/1987 | Card | |
| 5,569,262 A | * | 10/1996 | Carney | 606/96 |
| 5,817,098 A | * | 10/1998 | Albrektsson et al. | 606/96 |
| 5,919,196 A | | 7/1999 | Bobic et al. | |
| 6,146,385 A | * | 11/2000 | Torrie et al. | 606/96 |
| 6,395,011 B1 | * | 5/2002 | Johanson et al. | 606/179 |
| 6,482,182 B1 | * | 11/2002 | Carroll et al. | 604/174 |
| 6,488,033 B1 | | 12/2002 | Cerundolo | |
| 6,592,588 B1 | | 7/2003 | Bobic et al. | |
| 6,852,114 B2 | | 2/2005 | Cerundolo | |
| RE40,796 E | * | 6/2009 | O'Neill | 600/567 |
| 2002/0042624 A1 | * | 4/2002 | Johanson et al. | 606/179 |
| 2002/0068936 A1 | * | 6/2002 | Burkus et al. | 606/57 |
| 2003/0083666 A1 | * | 5/2003 | Zdeblick et al. | 606/90 |
| 2003/0199879 A1 | * | 10/2003 | Spranza, III | 606/79 |
| 2004/0127987 A1 | * | 7/2004 | Evans et al. | 623/11.11 |
| 2006/0009767 A1 | * | 1/2006 | Kiester | 606/61 |
| 2006/0178748 A1 | * | 8/2006 | Dinger et al. | 623/18.11 |

FOREIGN PATENT DOCUMENTS

EP    1 006 957 B1   11/2003

* cited by examiner

Primary Examiner — Thomas C Barrett
Assistant Examiner — Sameh Boles

(57) ABSTRACT

A method is disclosed and can include engaging a harvest guide with bony tissue and placing a cutting device within the harvest guide. The harvest guide can maintain the cutting device substantially perpendicular to a tangent through a point on the bony tissue aligned with the cutting device. The cutting device can be an osteochondral chisel, a trephine, or a combination thereof.

14 Claims, 51 Drawing Sheets

SYSTEM AND METHOD OF HARVESTING OSTEOCHONDRAL PLUGS

FIELD OF THE DISCLOSURE

The present disclosure relates generally to orthopedics and orthopedic surgery. More specifically, the present disclosure relates to harvesting osteochondral plugs and creating recipient sockets for square osteochondral plugs.

BACKGROUND

Osteochondral plugs can be used to treat cartilage defects in knee joints, hip joints, and ankle joints. For example, a recipient socket can be created in a bone to be treated and an osteochondral plug can be inserted in the recipient socket. The osteochondral plug can be harvested from a bone of a cadaver, e.g., a femur, a tibia, a fibula, etc. The osteochondral plug can be harvested by cutting the plug from the donor bone. To achieve the best results, the osteochondral plug should closely fit into the recipient socket. Further, the curvature of the upper surface of the plug should closely match the curvature of the bone into which the plug is installed. Obtaining a close match between the geometry of the plug and the geometry of the recipient socket and surrounding tissue can be difficult.

Accordingly, there is a need for a system and method for harvesting osteochondral plugs and creating recipient sockets.

DETAILED DESCRIPTION OF THE DRAWINGS

Figure 1:
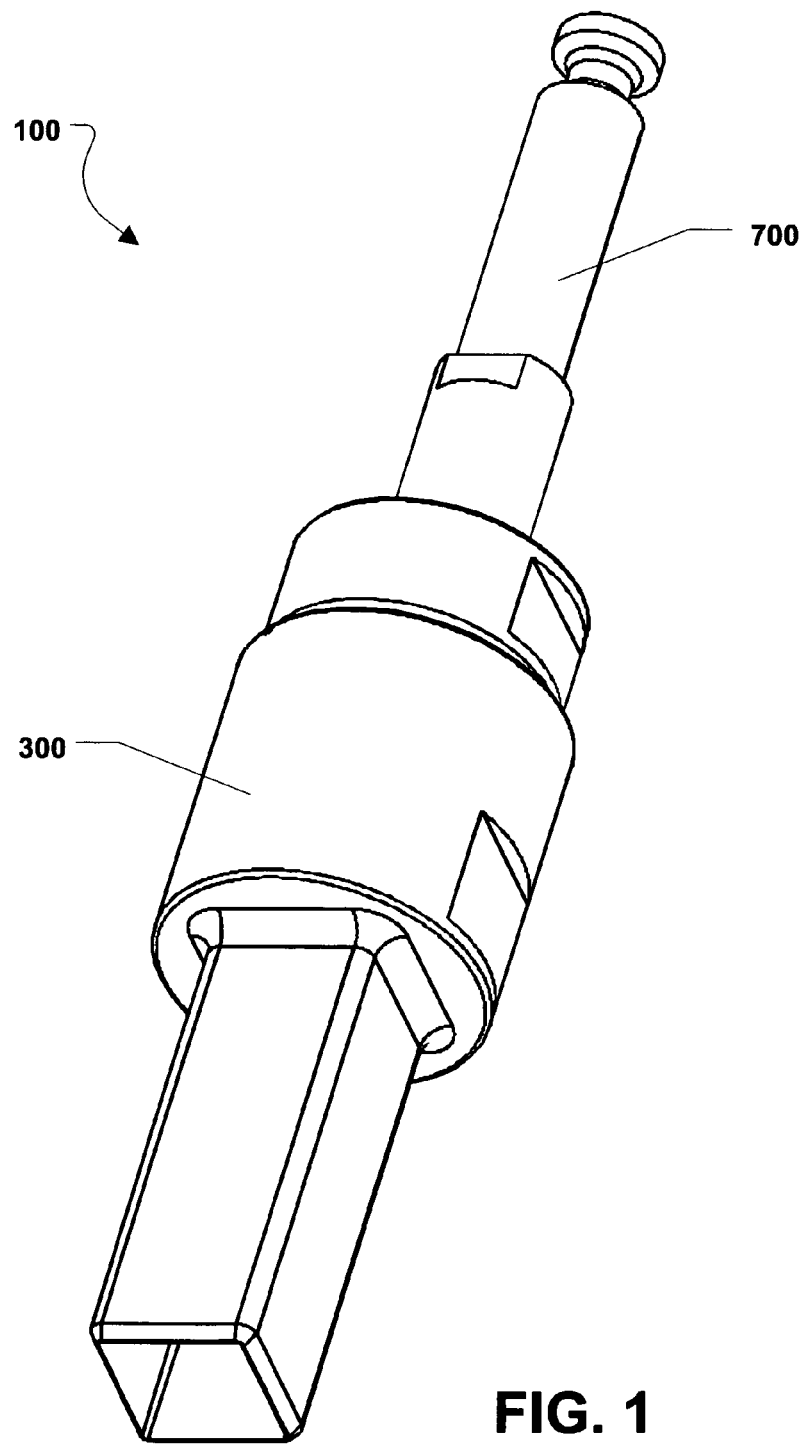
FIG. 1 is a perspective view of an osteochondral chisel assembly.

An osteochondral chisel is disclosed and can include a body that can have a proximal end and a distal end. A first portion can extend from the proximal end. Further, a second portion can extend from the distal end and can terminate at the first portion. The second portion can be hollow and can include an internal cavity. The second portion can be driven linearly into tissue in order to create a plug having a shape that substantially matches the internal cavity of the second portion of the body.

In another embodiment, an osteochondral chisel adapter is disclosed and can include a post that can have a proximal end and a distal end. An enlarged head can extend from the distal end of the post. The enlarged head can engage an internal cavity formed in an osteochondral chisel.

In yet another embodiment, an osteochondral chisel assembly is disclosed and can include an osteochondral chisel and an osteochondral chisel adapter. The osteochondral chisel adapter can engage the osteochondral chisel and a linear actuator device.

In still another embodiment, a harvest guide for a cutting device is disclosed and can include a body having a top and a bottom. Further, the harvest guide can include an interior cavity formed within the body from the top to the bottom. The interior cavity can receive the cutting device.

In yet still another embodiment, an orientation guide for a harvest guide is disclosed and can include a body that can have a top and a bottom. A first foot can extend from the bottom of the body. A second foot can also extend from the bottom of the body. Further, a third foot can extend from the bottom of the body. The orientation guide can rest on bony tissue. Moreover, the first foot, the second foot and the third foot can be configured such that the orientation guide can be properly oriented when all three of the first foot, the second foot and the third foot are in simultaneous contact with the bony tissue.

In another embodiment, an impactor is disclosed and can include a shaft that can have a proximal end and a distal end. A harvest guide cap can extend from the distal end of the shaft. The harvest guide cap can be configured to fit around a harvest guide that is configured to receive a cutting device.

In still another embodiment, a harvest guide assembly is disclosed and can include a harvest guide that can have an internal cavity. Also, the harvest guide can be driven into bony tissue. The harvest guide assembly can also include an orientation guide that can fit into the internal cavity of the harvest guide. The orientation guide can be used to orient the harvest guide relative to bony tissue.

In yet still another embodiment, a method is disclosed and can include engaging a harvest guide with bony tissue and placing a cutting device within the harvest guide. The harvest guide can maintain the cutting device substantially perpendicular to a tangent through a point on the bony tissue aligned with the cutting device.

Description of an Osteochondral Chisel Assembly

Figure 2:
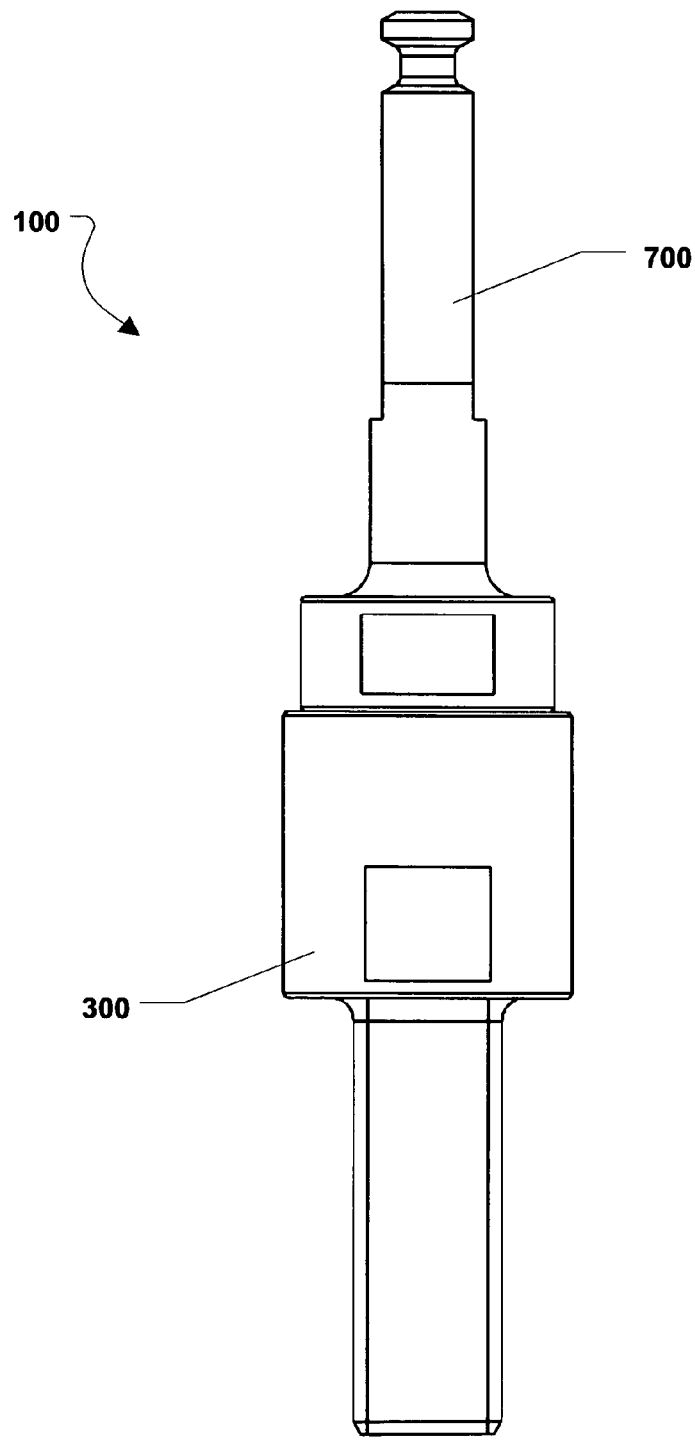
FIG. 2 is a plan view of an osteochondral chisel assembly.

Referring initially to FIG. 1 and FIG. 2, an osteochondral chisel assembly is shown and is generally designated 100. As illustrated, the osteochondral chisel assembly 100 can include an osteochondral chisel 300 and an osteochondral chisel adapter 700. As described in greater detail below, the osteochondral chisel 300 can fit into the osteochondral chisel adapter 700.

Description of the Osteochondral Chisel

FIG. 3 through FIG. 6 illustrate the details of the osteochondral chisel 300. As shown the osteochondral chisel 300 can include a body 302. The body 302 can include a proximal end 304 and a distal end 306. Additionally, the body 302 can include a first portion 308 near the proximal end 304 of the body 302. Further, the body 302 can include a second portion 310 that extends from the first portion 308 and terminates at the distal end 306.

In a particular embodiment, the first portion 308 of the body 302 can be generally cylindrical. Further, the first portion 308 of the body 302 can be formed with an internal cavity 312 that can extend into the first portion 308 from the proximal end 304 of the body 302. As described below, the osteochondral chisel adapter 700 can fit into the internal cavity 312 formed in the first portion 308 of the body 302.

Figure 3:
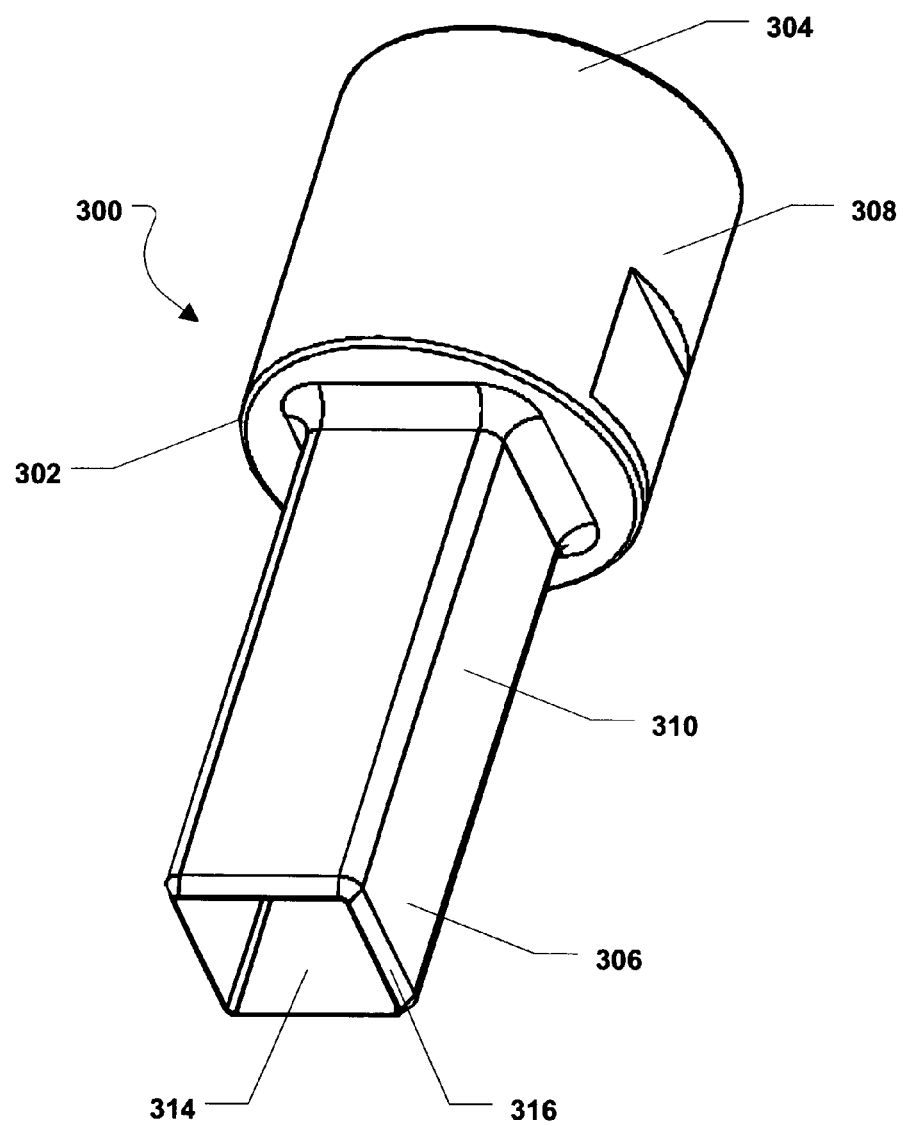
FIG. 3 is a perspective view of an osteochondral chisel.
Figure 4:
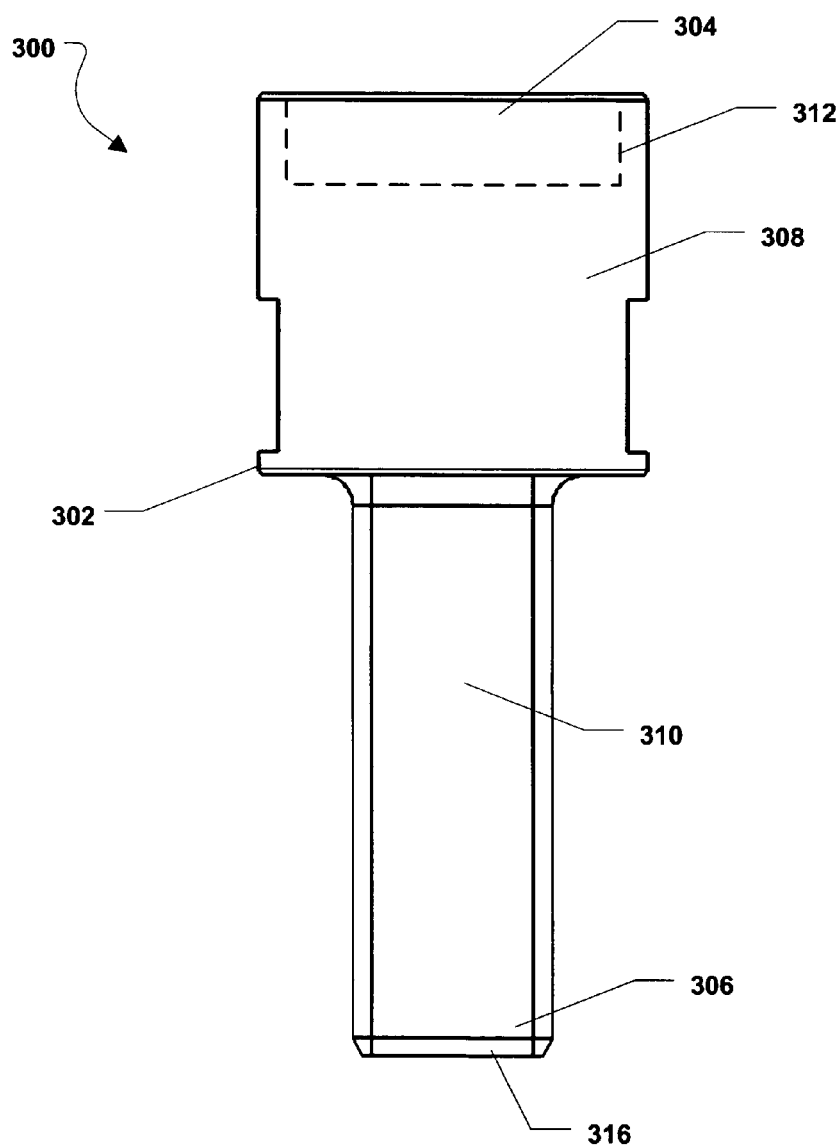
FIG. 4 is a first lateral plan view of the osteochondral chisel.
Figure 5:
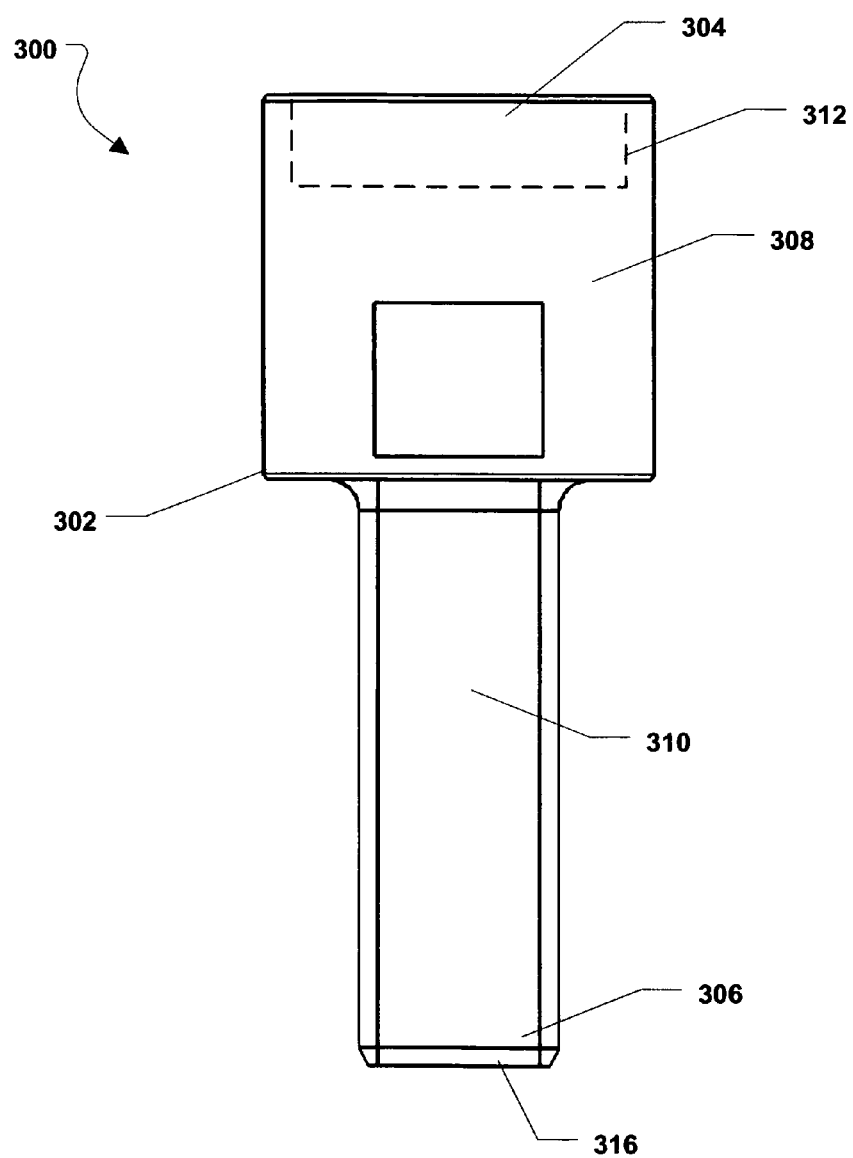
FIG. 5 is a second lateral plan view of the osteochondral chisel.
Figure 6:
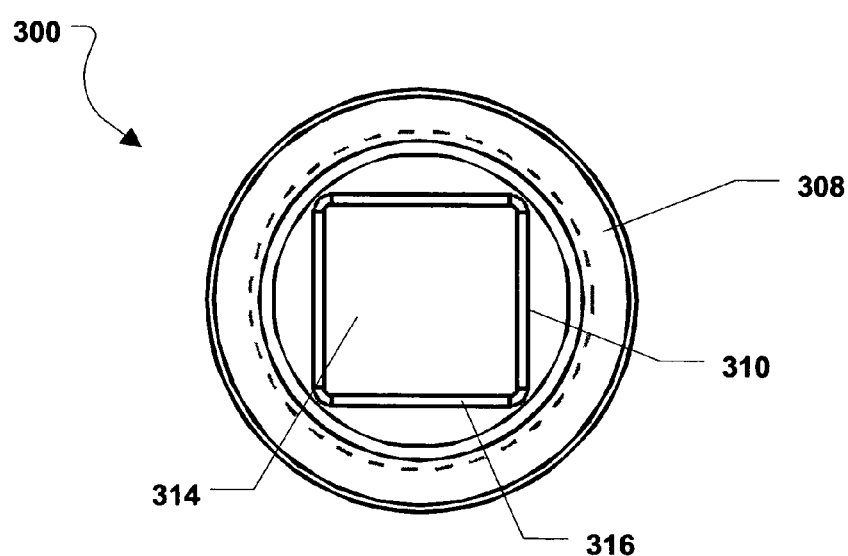
FIG. 6 is an end plan view of the osteochondral chisel.

As shown in FIG. 3, the second portion 310 of the body 302 can be hollow and generally prismatic. In particular, the second portion 310 can be a prism having a generally square cross-section. More specifically, the second portion 310 can be a parallelepiped having a generally square cross-section. Further, as depicted in FIG. 3, the second portion 310 of the body 302 can include an internal cavity 314. Also, the second portion 310 of the body 302 can include a cutting edge 316 formed at the distal end 306 of the body 302. The osteochondral chisel 300 can be driven into tissue, e.g., bone, to create an osteochondral plug. Further, the osteochondral chisel 300 can be driven into tissue, e.g., bone, to create a recipient socket for an osteochondral plug.

Description of the Osteochondral Chisel Adapter

Figure 7:
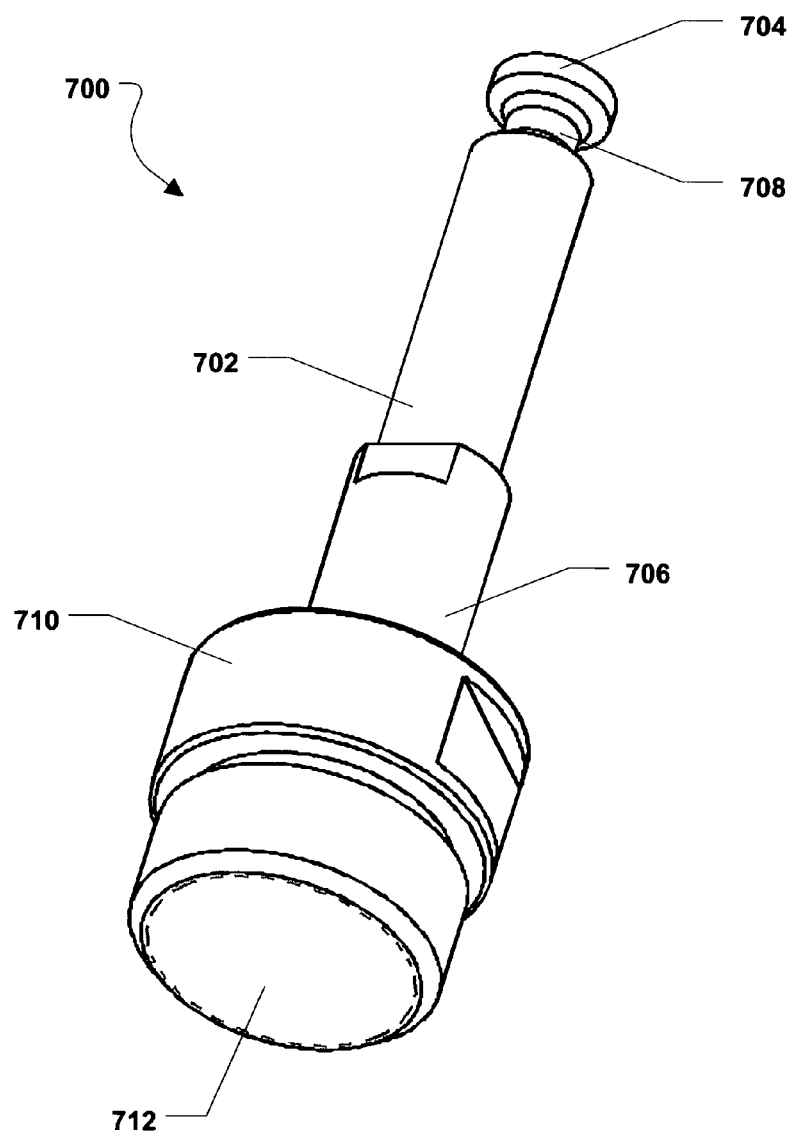
FIG. 7 is a perspective view of an osteochondral chisel adapter.
Figure 8:
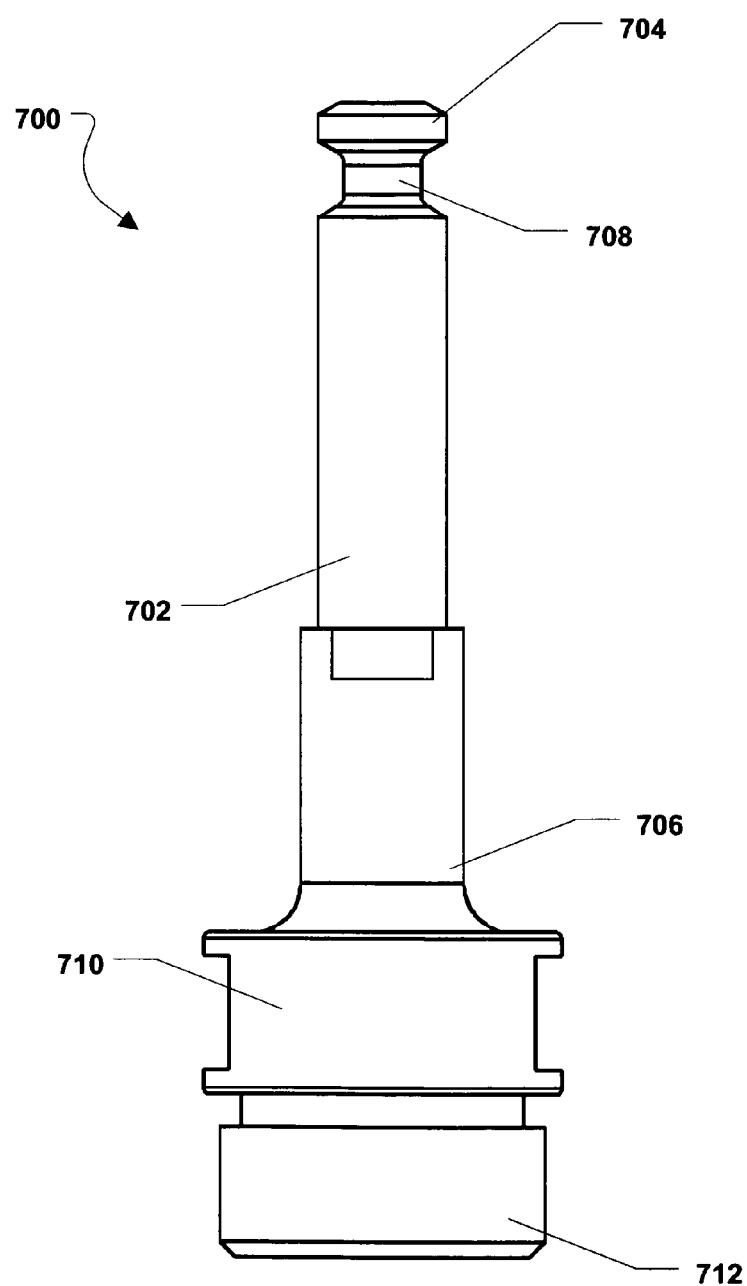
FIG. 8 is a first lateral plan view of the osteochondral chisel adapter.
Figure 9:
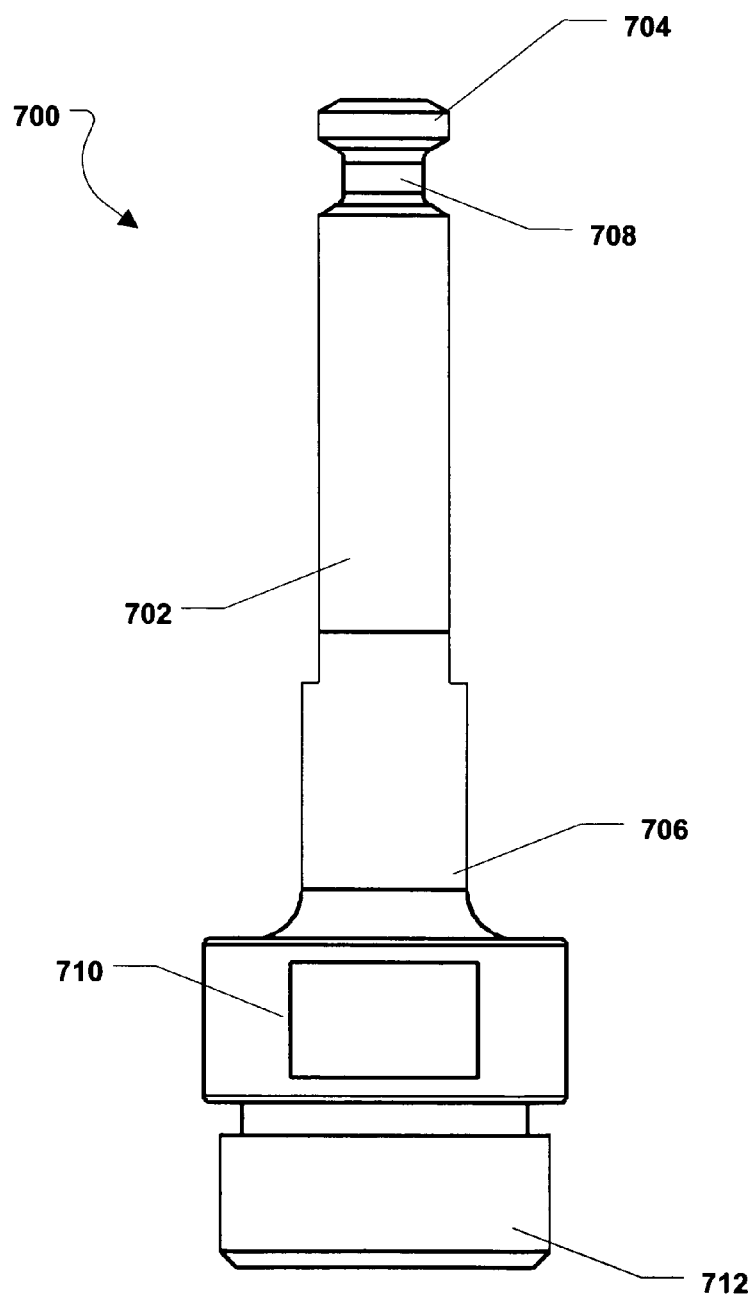
FIG. 9 is a second lateral plan view of the osteochondral chisel adapter.

Referring to FIG. 7 through FIG. 9, the osteochondral chisel adapter 700 is shown. The osteochondral chisel adapter 700 can include a post 702 having a proximal end 704 and a distal end 706. The post 702 can be generally cylindrical. Moreover, as shown in FIG. 7 through FIG. 9, the post 702 can include an annular groove 708 formed near the proximal end 704 of the post 702.

The osteochondral chisel adapter 700 can also include an enlarged head 710 that can be coupled to the distal end 706 of the post 702. The enlarged head 712 can be generally cylindrical. Further, the enlarged head 712 can include an osteochondral chisel engagement portion 712. In a particular embodiment, the osteochondral chisel engagement portion 712 is sized and shaped to fit into the internal cavity 312 formed in the first portion 308 of the body 302 of the osteochondral chisel 300, shown in FIG. 3 through FIG. 6.

Description of a First Embodiment of a Harvest Guide Assembly

Figure 10:
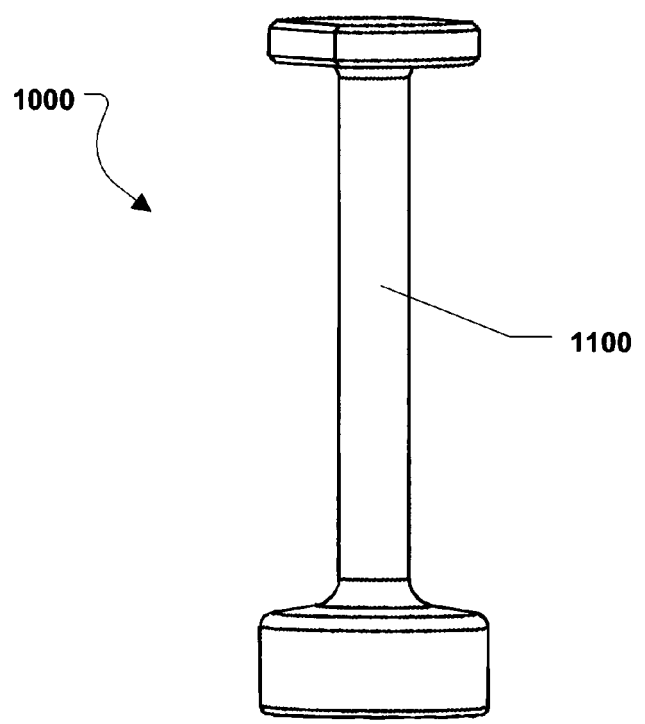
FIG. 10 is a plan view of a first embodiment of a harvest guide assembly.
Figure 10:
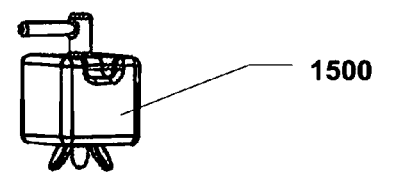
Figure 10:
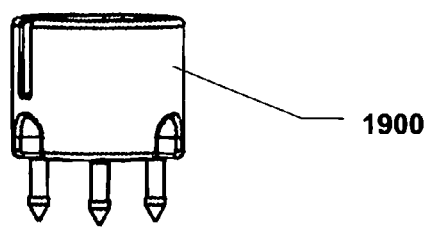
Figure 11:
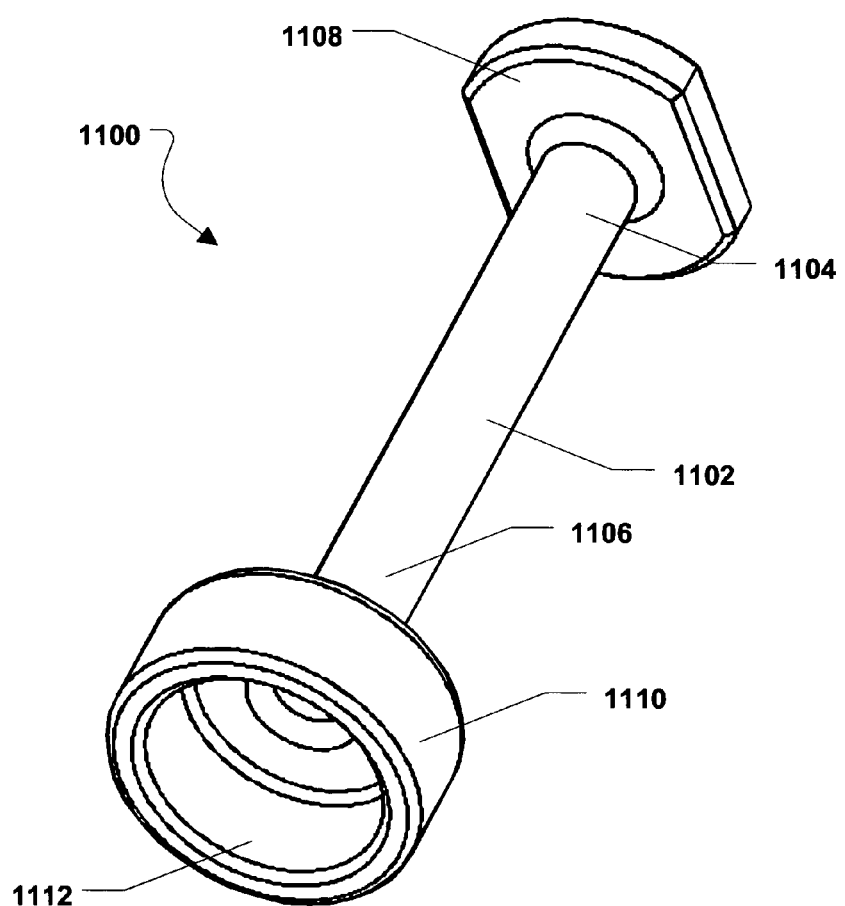
FIG. 11 is a perspective view of an impactor associated with the first harvest guide assembly.
Figure 12:
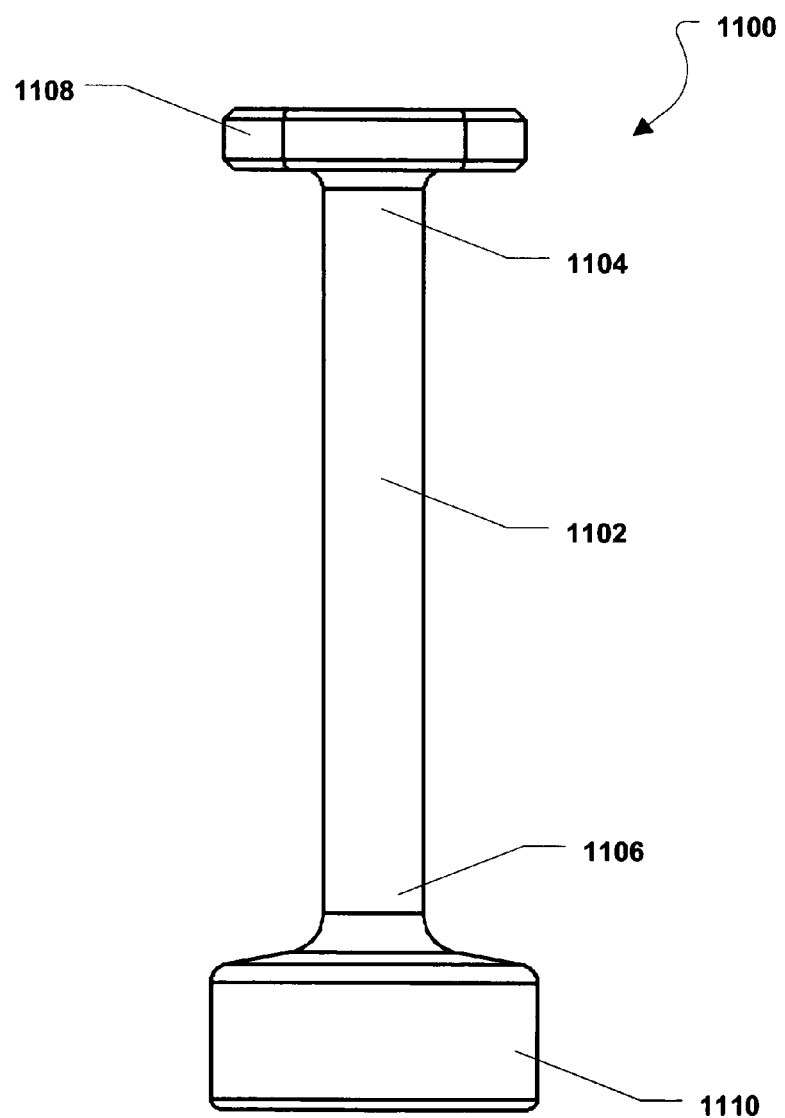
FIG. 12 is a first lateral plan view of the impactor.
Figure 13:
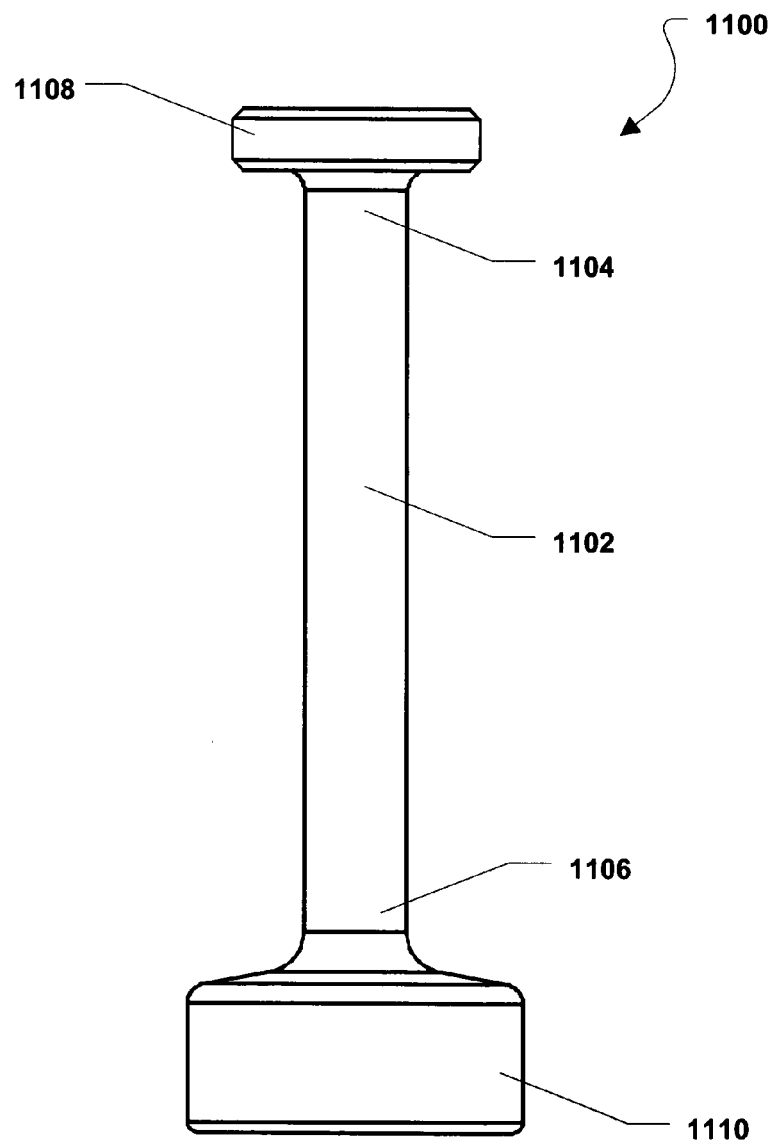
FIG. 13 is a second lateral plan view of the impactor.
Figure 14:
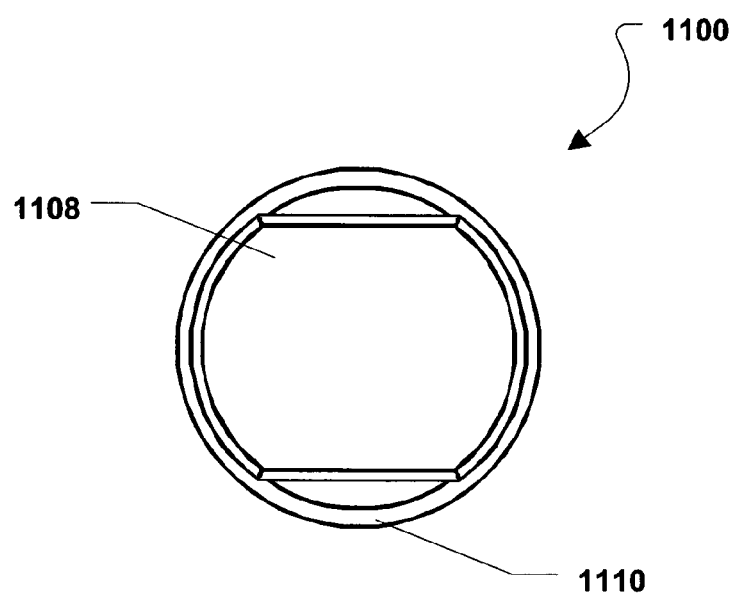
FIG. 14 is an end plan view of the impactor.
Figure 15:
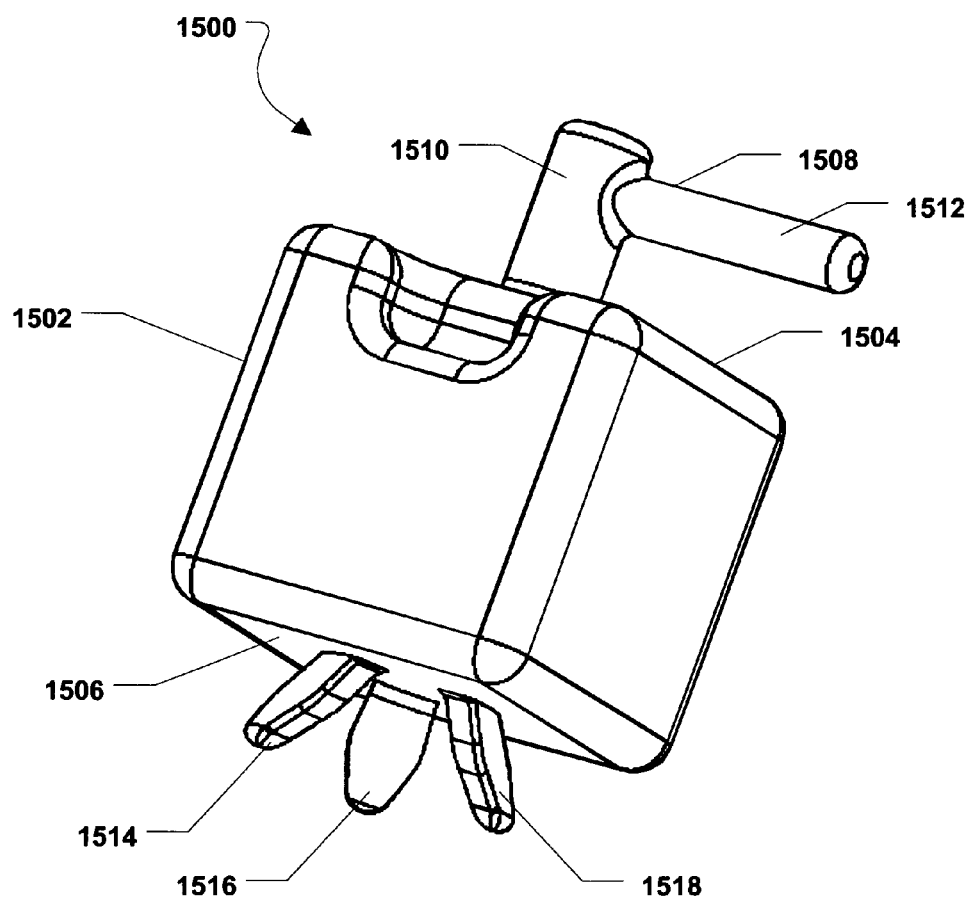
FIG. 15 is a perspective view of an orientation guide associated with the first harvest guide assembly.
Figure 16:
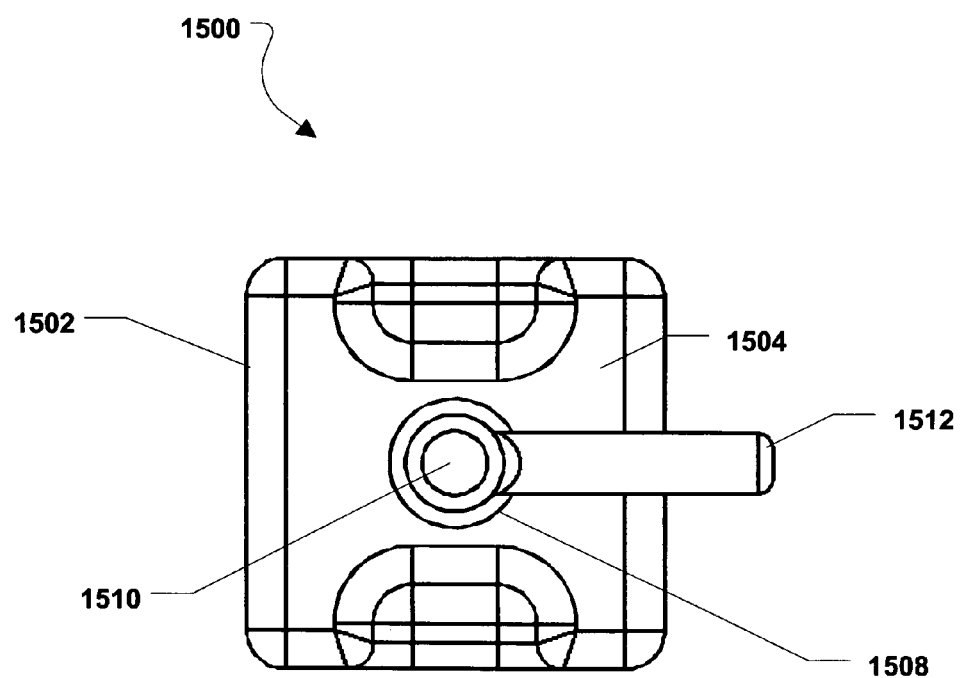
FIG. 16 is a top plan view of the orientation guide.
Figure 17:
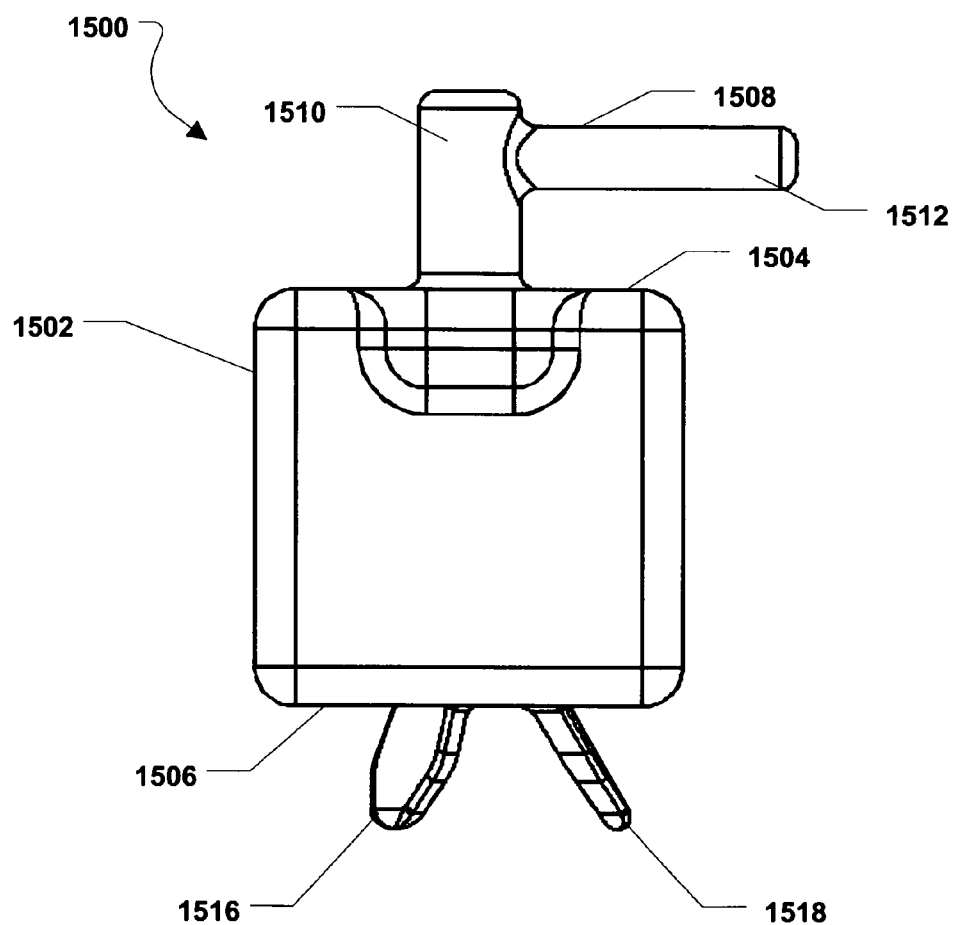
FIG. 17 is a first lateral plan view of the orientation guide.
Figure 18:
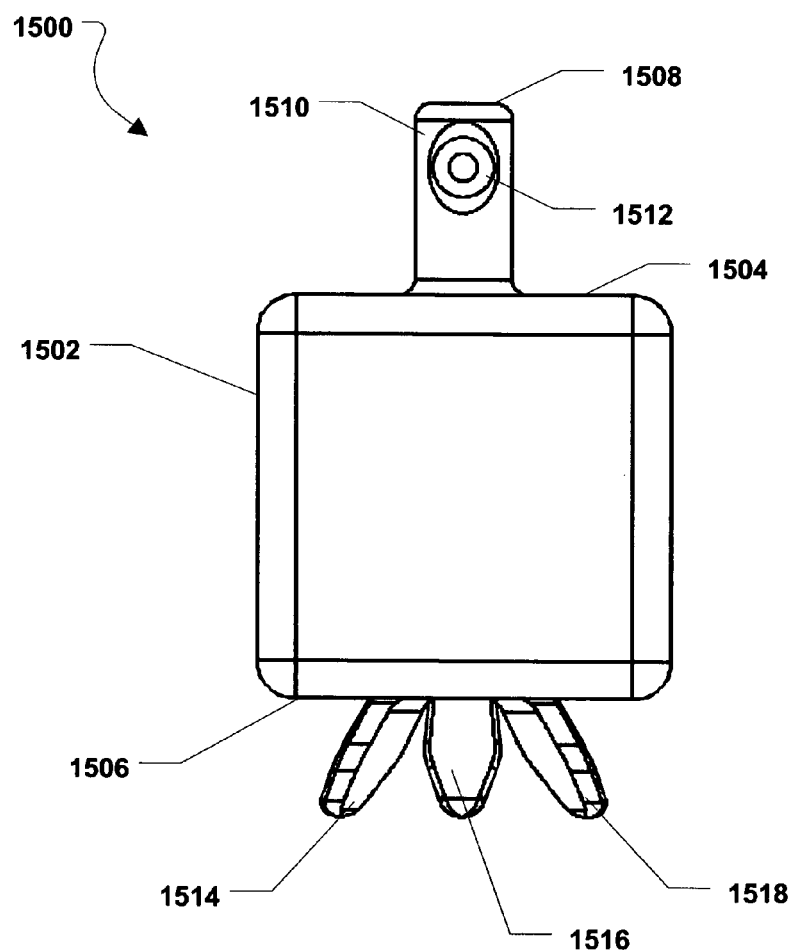
FIG. 18 is a second lateral plan view of the orientation guide.
Figure 19:
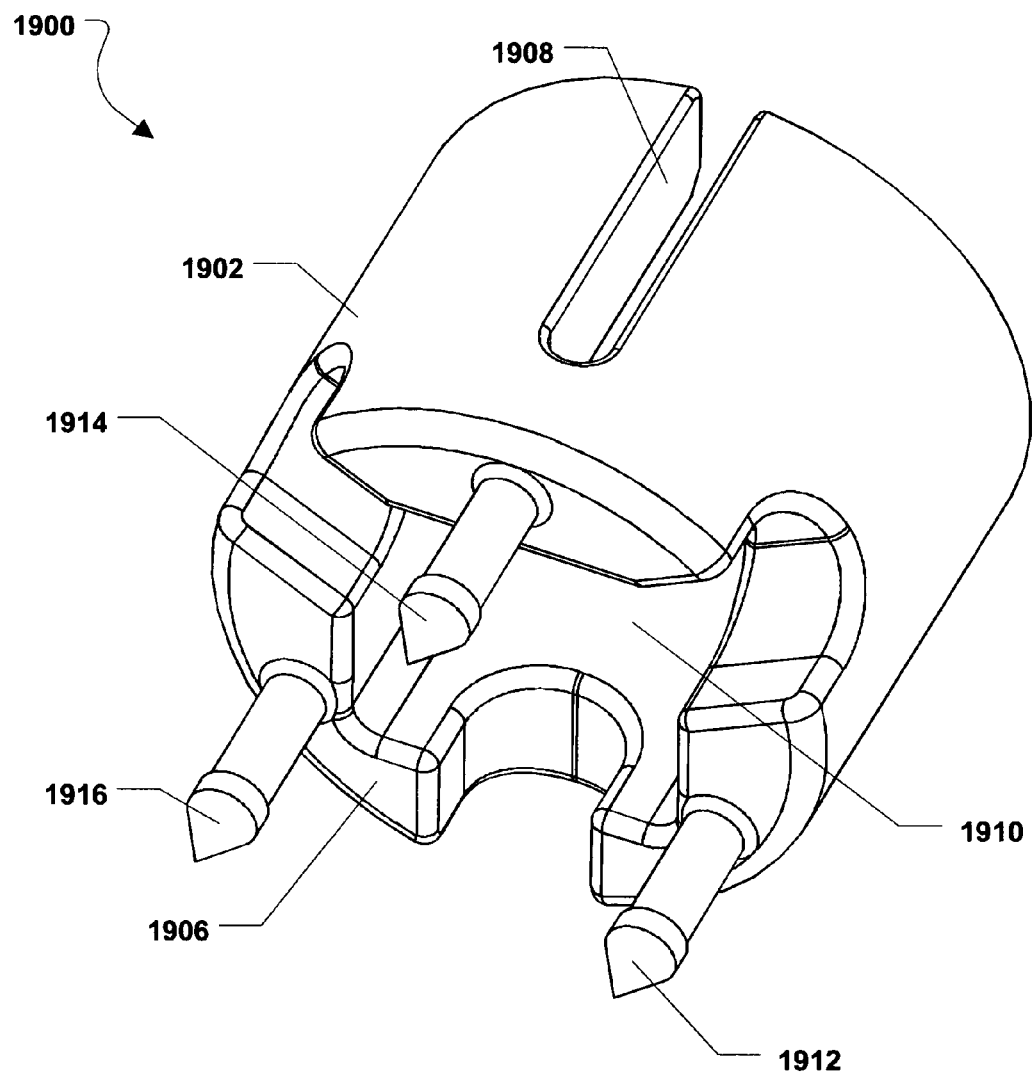
FIG. 19 is a perspective view of a harvest guide associated with the first harvest guide assembly.
Figure 20:
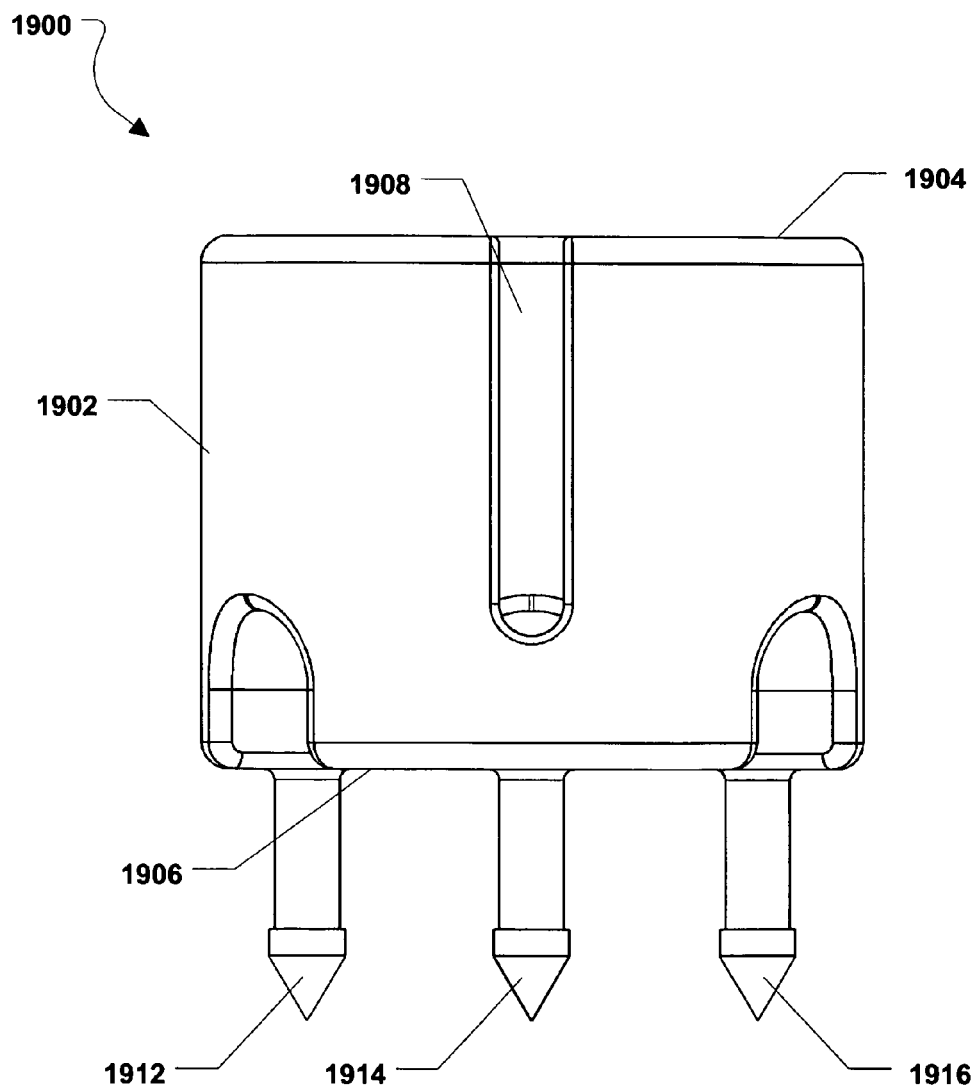
FIG. 20 is a first lateral plan view of the harvest guide.
Figure 21:
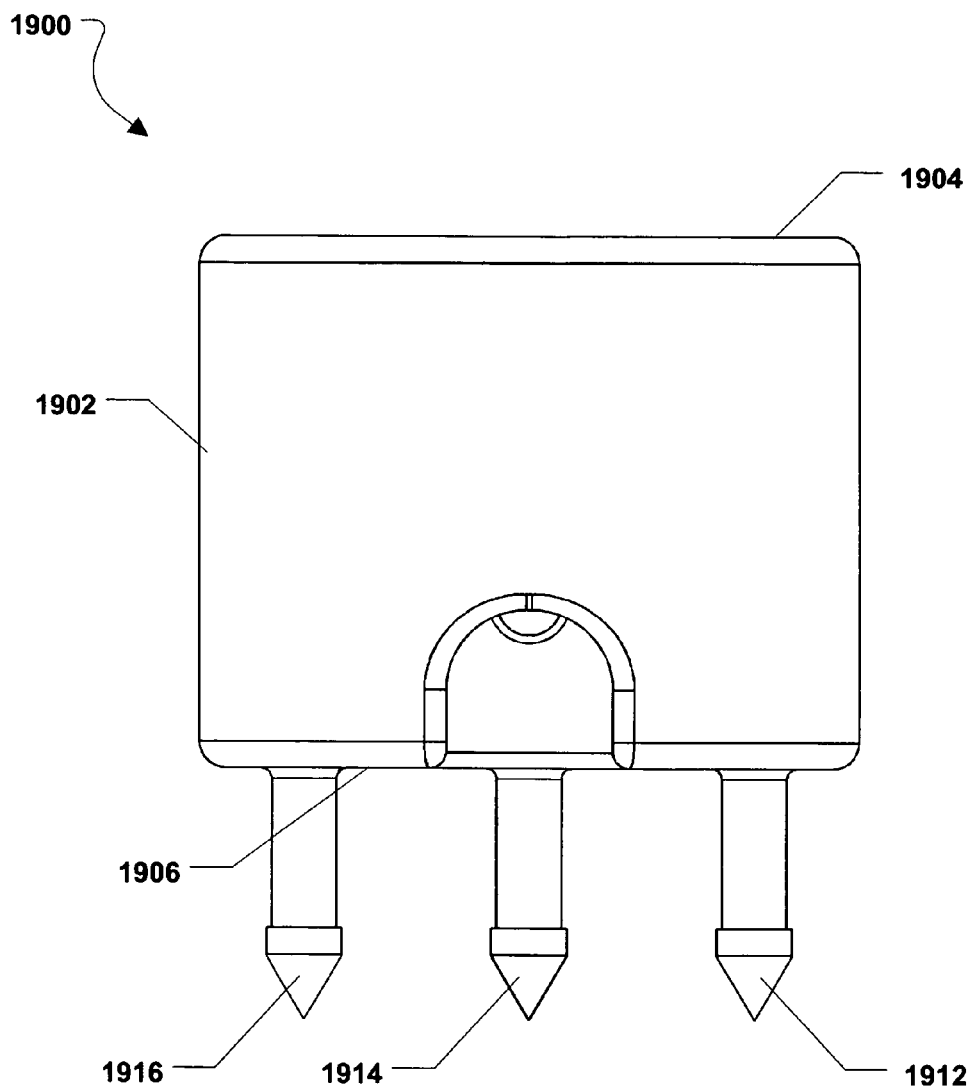
FIG. 21 is a second lateral plan view of the harvest guide.
Figure 22:
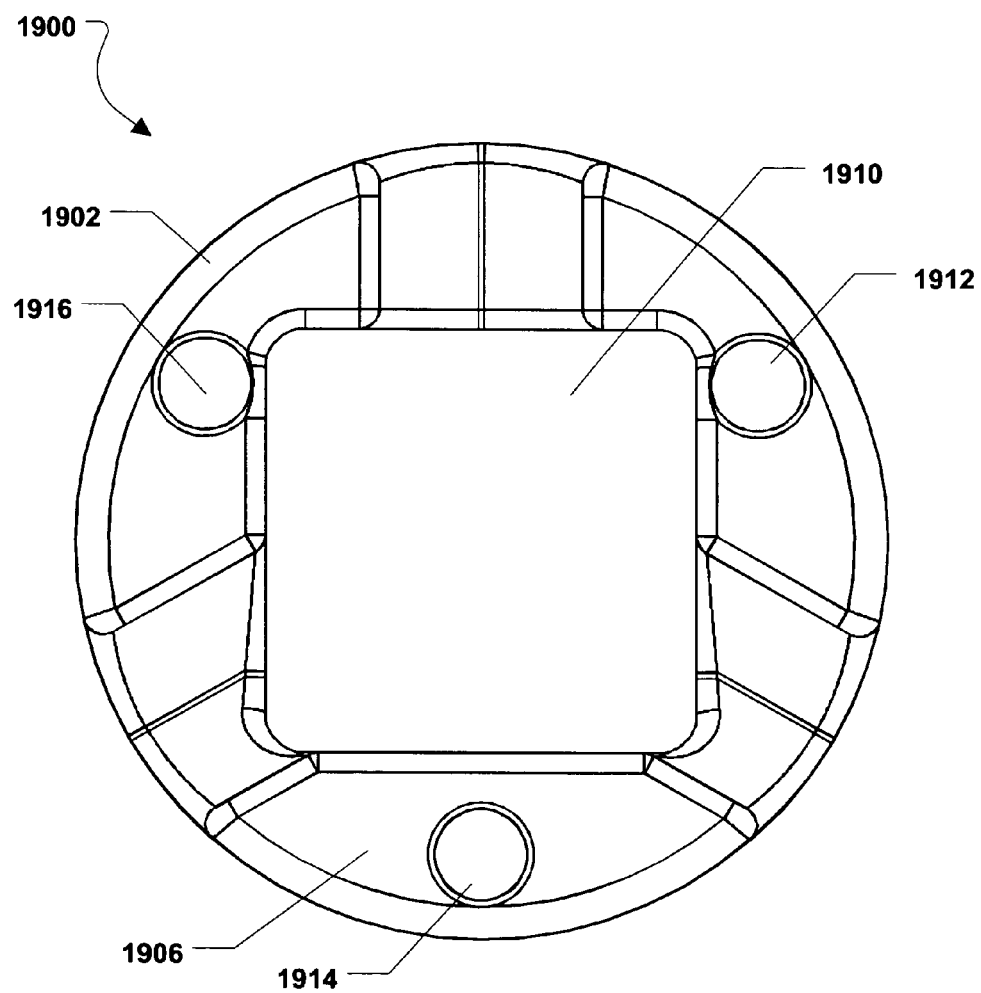
FIG. 22 is a top plan view of the harvest guide.

Referring to FIG. 10, a harvest guide assembly is shown and is generally designated 1000. As depicted in FIG. 10, the harvest guide assembly 1000 can include an impactor 1100, an orientation guide 1500, and a harvest guide 1900.

Description of an Impactor Associated with the First Harvest Guide Assembly

Referring to FIG. 11 through FIG. 14, details concerning the impactor 1100 can be seen. As illustrated, the impactor 1100 can include a shaft 1102 that can have a proximal end 1104 and a distal end 1106. Further, an impact plate 1108 can be coupled, or otherwise connected, to the proximal end 1104 of the shaft 1102. FIG. 11 through FIG. 14 also indicate that a harvest guide cap 1110 can be coupled, or otherwise connected, to the distal end 1106 of the shaft 1102. The harvest guide cap 1110 can include an internal cavity 1112 that can be sized and shaped to fit around the harvest guide 1900 (FIG. 10), described in detail below. In a particular embodiment, the impact plate 1108 and the harvest guide cap 1110 can be integrally formed with the shaft 1102.

During use, the impactor 1100 can be placed around the harvest guide 1900 (FIG. 10). Moreover, a hammer can be used to strike the impact plate 1108. The shaft 1102 can transmit the impact from the hammer to the harvest guide cap 1110. Further, the harvest guide cap 1110 can transmit the impact to the harvest guide 1900 (FIG. 10) and the harvest guide 1900 can be driven into a condyle.

Description of an Orientation Guide Associated with the First Harvest Guide Assembly Referring to FIG. 15 through FIG. 18, details concerning the orientation guide 1500 can be seen. As depicted, the orientation guide 1500 can include a generally cubic body 1502. The body 1502 can include a top surface 1504 and a bottom surface 1506. Further, a handle 1508 can extend from the top surface 1504 of the body 1502. The handle 1508 can include a first portion 1510 that can be generally perpendicular to the top surface 1504 of the body 1502. Also, the handle 1508 can include a second portion 1512 that can extend substantially perpendicular from the first portion 1510 of the handle 1508. The second portion 1512 of the handle 1508 can also be substantially parallel to the top surface 1504 of the body 1502.

FIG. 15 through FIG. 18 also show that the orientation guide 1500 can include a first foot 1514, a second foot 1516, and a third foot 1518 extending from the bottom surface 1506 of the body 1502. In a particular embodiment, each foot 1514, 1516, 1518 can extend from the bottom surface 1506 at an angle relative to the bottom surface 1506. Accordingly, in a particular embodiment, the orientation guide 1500 can be an orientation tripod having three feet on which the orientation tripod can rest.

During use, the orientation guide 1500 can be fitted into the harvest guide 1900 (FIG. 10). Further, the orientation guide 1500 and harvest guide 1900 (FIG. 10) can be placed on a rounded surface of a condyle. The orientation guide 1500, e.g., each foot 1514, 1516, 1518 thereof, can ensure proper placement and alignment of the harvest guide 1900 (FIG. 10) prior to the harvest guide 1900 (FIG. 10) being driven into the condyle, as described herein. After the harvest guide 1900 (FIG. 10) is driven into the condyle, the orientation guide 1500 can be removed from the harvest guide 1900 (FIG. 10).

When the orientation guide 1500 is placed within the harvest guide 1900 (FIG. 10), as described herein, the handle 1508 that extends from the body 1502 of the orientation guide 1500 can extend through a slot formed in the harvest guide 1900 (FIG. 10). In particular, the second portion 1512 of the handle 1508 can extend through the slot formed in the harvest guide 1900 (FIG. 10). The handle 1508 can facilitate placement of the orientation guide 1500 within the harvest guide 1900 (FIG. 10). Further, the handle 1508 can facilitate retrieval of the orientation guide 1500 from within the harvest guide 1900 (FIG. 10).

Description of a Harvest Guide Associated with the First Harvest Guide Assembly

Referring to FIG. 19 through FIG. 22, the details concerning the harvest guide 1900 can be seen. As shown, the harvest guide 1900 can include a generally cylindrical body 1902. The body 1902 can include a top 1904 and a bottom 1906. Further, the body 1902 can include a slot 1908 and an interior cavity 1910 formed therein. The slot 1908 can extend from the top 1904 of the body 1902 partially along the length of the body 1902. The interior cavity 1910 can be sized and shaped to receive the orientation guide 1500, i.e., the interior cavity can be generally cubic.

FIG. 19 through FIG. 22 further indicate that the harvest guide 1900 can include a first tissue engagement post 1912, a second tissue engagement post 1914, and a third tissue engagement post 1916. The tissue engagement posts 1912, 1914, 1916 can extend from the bottom 1906 of the body 1902. Further, the tissue engagement posts 1912, 1914, 1916 can extend substantially perpendicularly from the bottom 1906 of the body 1902.

As described herein, the orientation guide 1500 (FIG. 15 through FIG. 18) can fit into the internal cavity 1910 formed in the body 1902 of the harvest guide 1900. Further, the handle 1508 (FIG. 15 through FIG. 18) that extends from the body 1502 (FIG. 15 through FIG. 18) of the orientation guide 1500 (FIG. 15 through FIG. 18) can extend through the slot 1908 formed in the body 1902 of the harvest guide 1900. Additionally, after the harvest guide 1900 is driven into a condyle, as described herein, the tissue engagement posts 1912, 1914, 1916 can engage the condyle and prevent the harvest guide 1900 from moving relative to the condyle. Further, after the orientation guide 1500 (FIG. 15 through FIG. 18) is retrieved from within the harvest guide 1900, as described herein, the osteochondral chisel 300 (FIG. 3 through FIG. 6) can be placed within the harvest guide 1900 and driven into the condyle using a linear actuator device, e.g., a pneumatic linearly activated device. The osteochondral chisel 300 (FIG. 3 through FIG. 6) can be used to harvest an osteochondral plug and to create a recipient socket for an osteochondral plug.

Description of a First Embodiment of a Method of Harvesting Osteochondral Plugs

Figure 23:
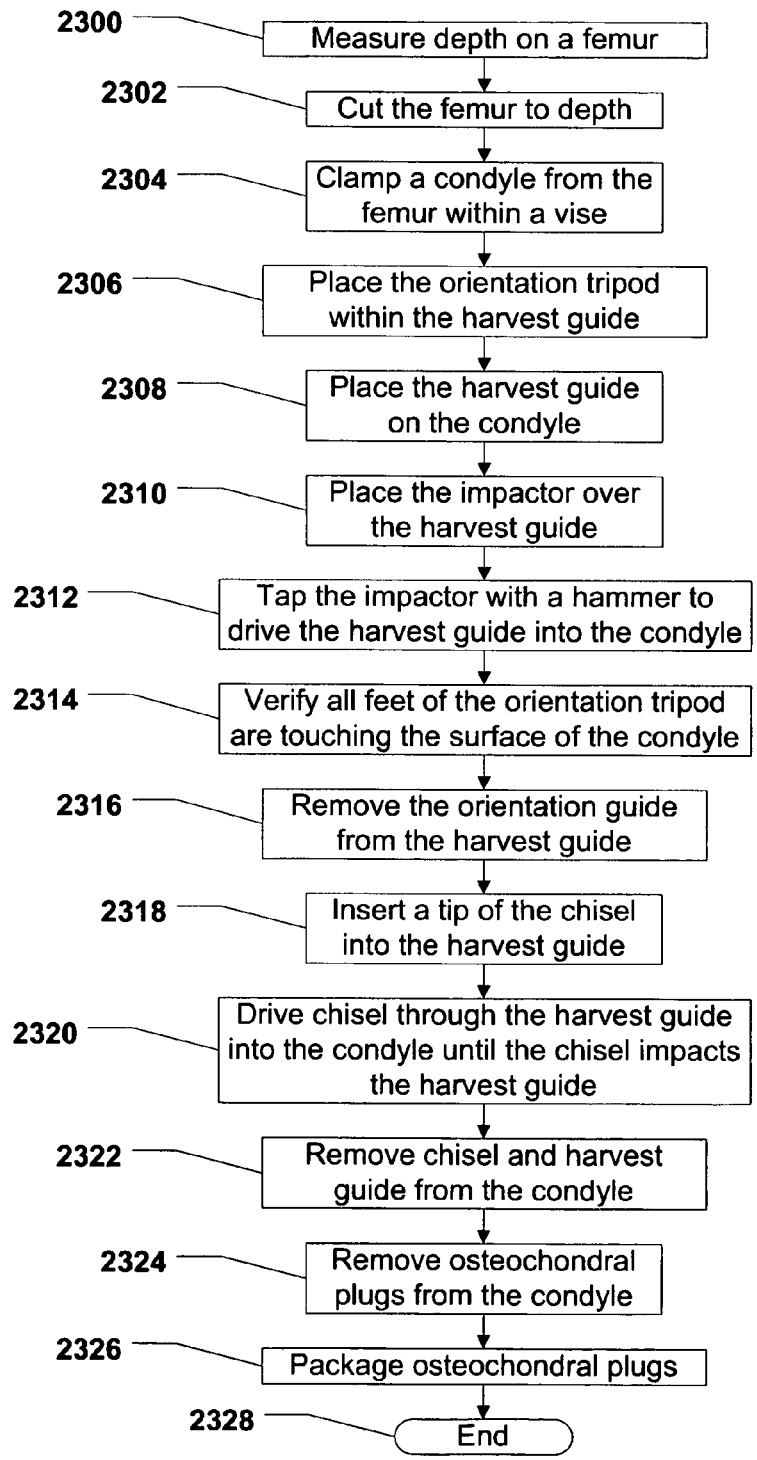
FIG. 23 is a flow chart illustrating a first method of harvesting an osteochondral plug.

FIG. 23 illustrates a flow chart of a first embodiment of a method of harvesting osteochondral plugs from bony tissue, e.g., from a condyle of a femur. FIG. 24 through FIG. 38 are a series of photographs chronicling an exemplary, non-limiting execution of the method of harvesting osteochondral plugs. For clarity, the method depicted in FIG. 23 will be described with continued reference to FIG. 23 and periodic reference to the photos shown in FIG. 24 through FIG. 38. In a particular embodiment, the osteochondral plugs can be harvested using an osteochondral chisel assembly and a harvest guide assembly according to one or more of the embodiments described herein. The osteochondral chisel assembly can include an osteochondral chisel and an osteochondral chisel adapter, described herein. Further, the harvest guide assembly can include an impactor, an orientation guide, and a harvest guide, described herein.

Figure 24:
FIG. 24 is a photograph illustrating a first step of the method.
Figure 25:
FIG. 25 is a photograph illustrating a second step of the method.
Figure 26:
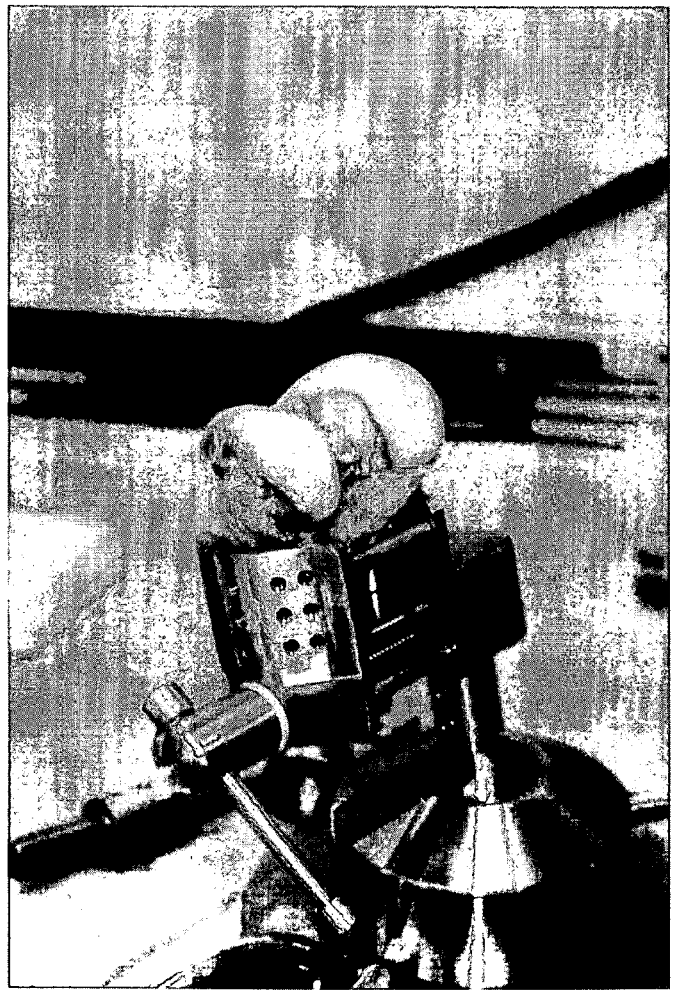
FIG. 26 is a photograph illustrating a third step of the method.

Commencing at block 2300 in FIG. 23, a depth on a femur can be measured. For example, as shown in FIG. 24, the depth on the femur can be measured using a stainless ruler and marked using a pencil. At block 2302 of FIG. 23, the femur can be cut to depth. As shown in FIG. 25, the femur can be cut to depth using a band saw. Alternatively, the femur can be cut to depth using a reciprocating saw or some other sharp bladed implement. Moving to block 2304 of FIG. 23, a condyle cut from the femur can be clamped within a vise, as depicted in FIG. 26.

Figure 27:
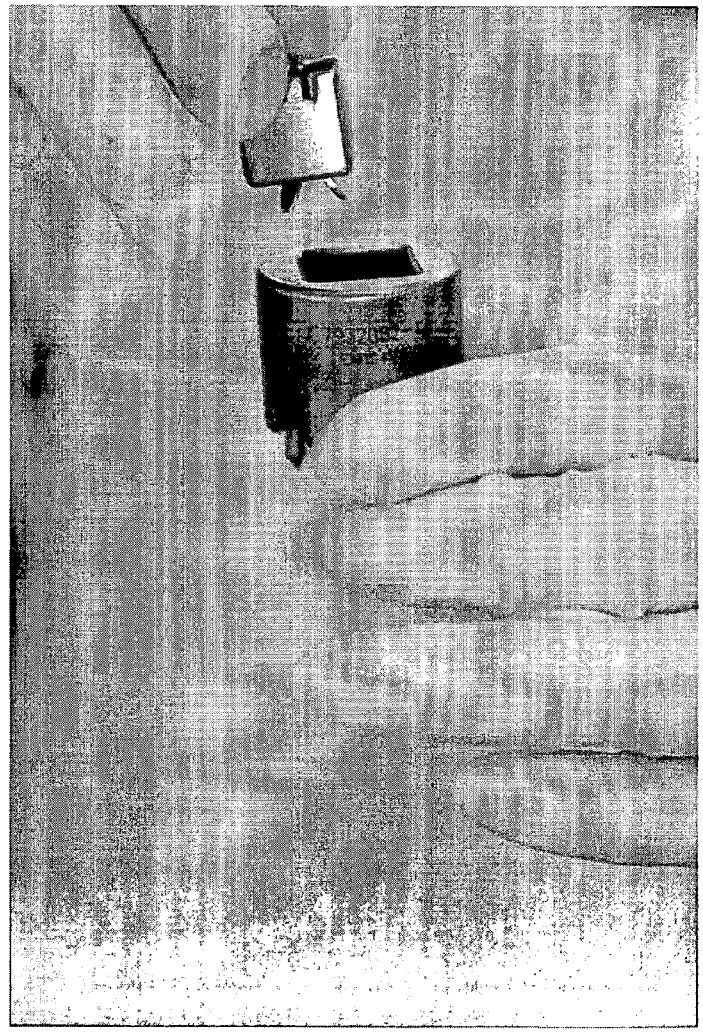
FIG. 27 is a photograph illustrating a fourth step of the method.
Figure 28:
FIG. 28 is a photograph illustrating a fifth step of the method.
Figure 29:
FIG. 29 is a photograph illustrating a sixth step of the method.
Figure 30:
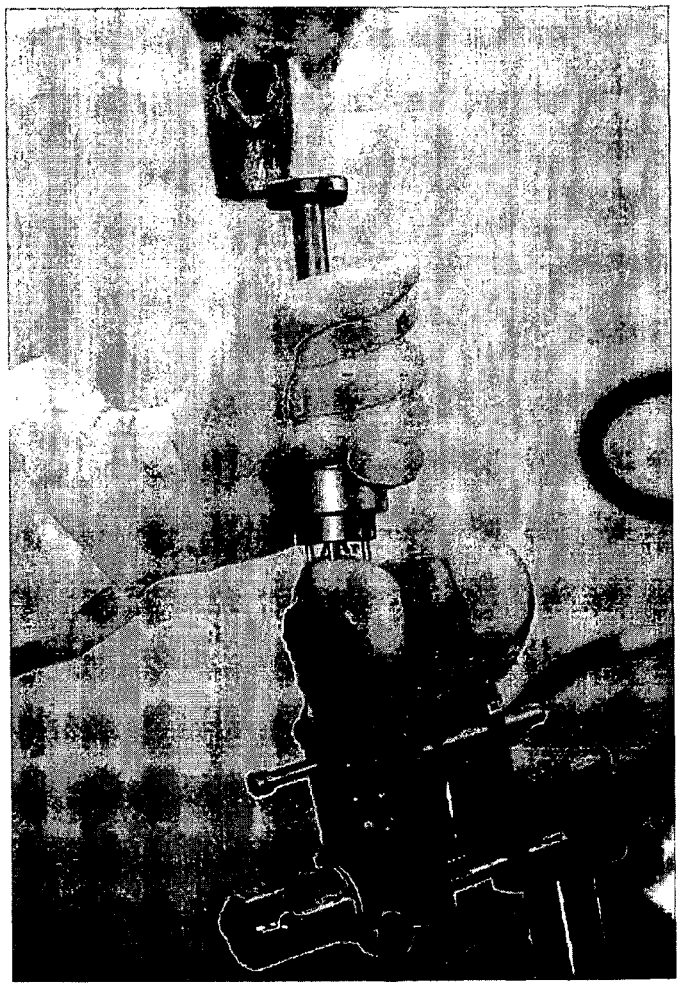
FIG. 30 is a photograph illustrating a seventh step of the method.

At block 2306, the orientation guide can be placed within the harvest guide, as shown in FIG. 27. Moreover, at block 2308 of FIG. 23, the harvest guide and orientation guide assembly can be placed on the condyle, as shown in FIG. 28. At block 2310 of FIG. 23, the impactor can be placed over the harvest guide, as depicted in FIG. 29. Further, at block 2312 of FIG. 23, the impactor can be tapped with a hammer, as shown in FIG. 30, in order to drive the harvest guide into the condyle.

Figure 31:
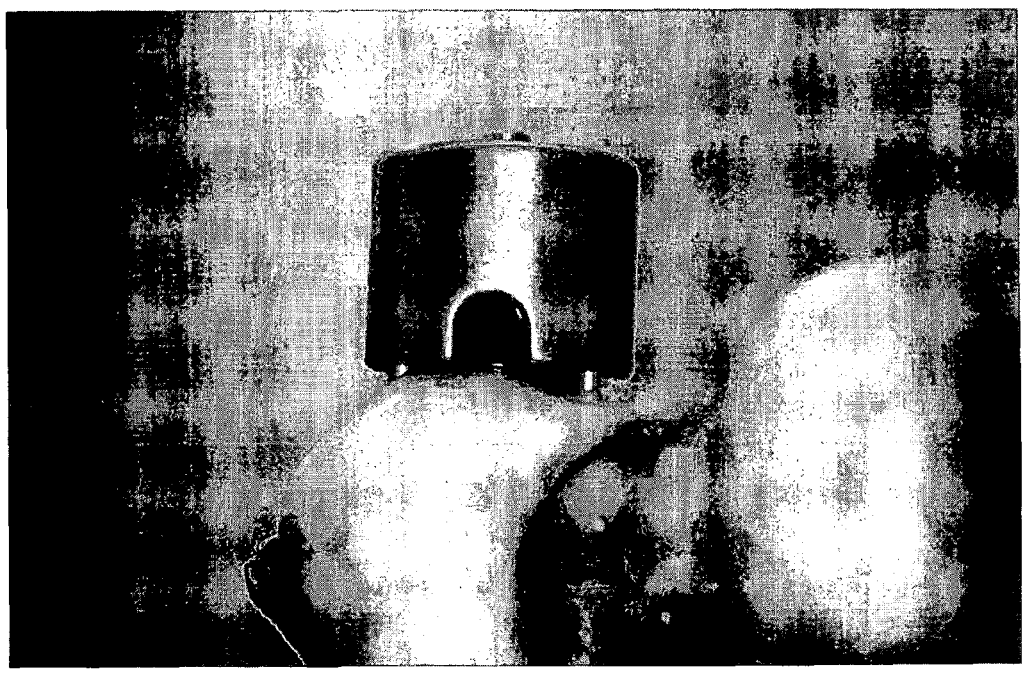
FIG. 31 is a photograph illustrating an eighth step of the method.
Figure 32:
FIG. 32 is a photograph illustrating a ninth step of the method.

Continuing to block 2314 of FIG. 23, a user, e.g., a surgeon, can verify that all of the feet extending from the orientation guide are touching the surface of the condyle, as depicted in FIG. 31. If one or more of the feet is not touching the surface of the condyle, the harvest guide can be removed and re-engaged with the surface of the condyle, as described above. On the other hand, if each of the feet is touching the surface of the condyle, the method can continue to block 2316 of FIG. 23 and the orientation guide can be removed from the harvest guide, as shown in FIG. 32.

Figure 33:
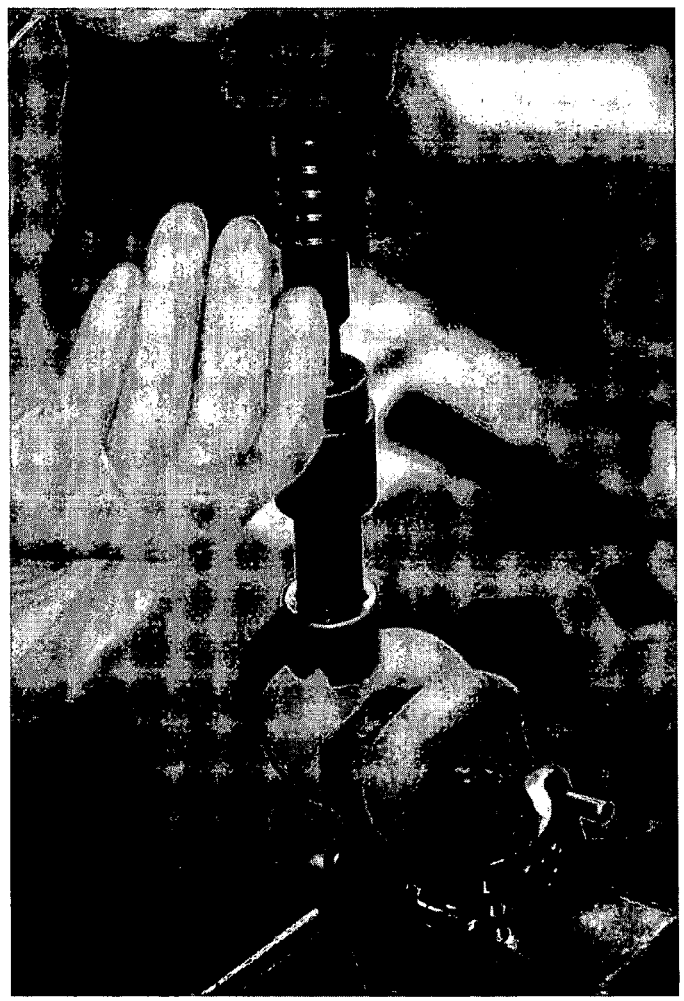
FIG. 33 is a photograph illustrating a tenth step of the method.
Figure 34:
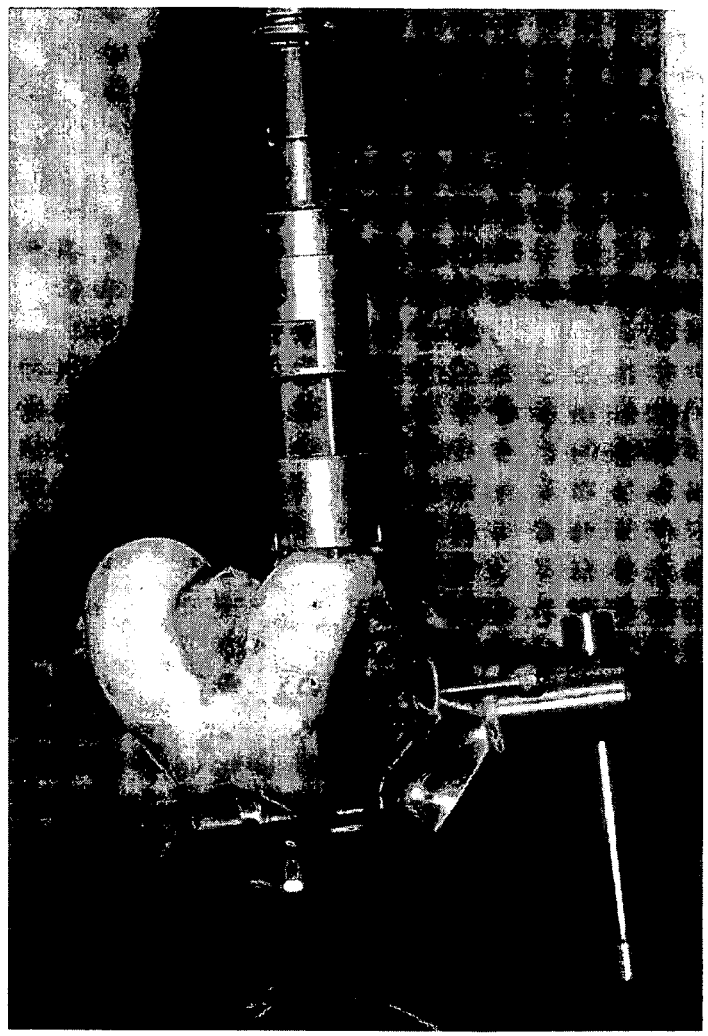
FIG. 34 is a photograph illustrating an eleventh step of the method.

At block 2318 of FIG. 23, and as shown in FIG. 33, the osteochondral chisel can be inserted into the harvest guide. The harvest guide, when properly placed, can maintain the osteochondral chisel substantially perpendicular to a tangent through a point on the bony tissue aligned with the osteochondral chisel. Particularly, the harvest guide can maintain the osteochondral chisel substantially perpendicular to a tangent through a point on the bony tissue that is aligned with a longitudinal axis of the osteochondral chisel. Thereafter, at block 2320, the osteochondral chisel can be driven through the harvest guide into the condyle, as depicted in FIG. 34. In a particular embodiment, the osteochondral chisel can be driven into the harvest guide until the chisel impacts the harvest guide. Further, in a particular embodiment, the osteochondral chisel can be driven into the harvest guide using a pneumatic linear actuator device. The osteochondral chisel can cut a perimeter surface of the osteochondral plug.

Figure 35:
FIG. 35 is a photograph illustrating a twelfth step of the method.
Figure 36:
FIG. 36 is a photograph illustrating a condyle with a plurality of osteochondral plugs formed therein.
Figure 37:
FIG. 37 is a photograph illustrating a thirteenth step of the method.
Figure 38:
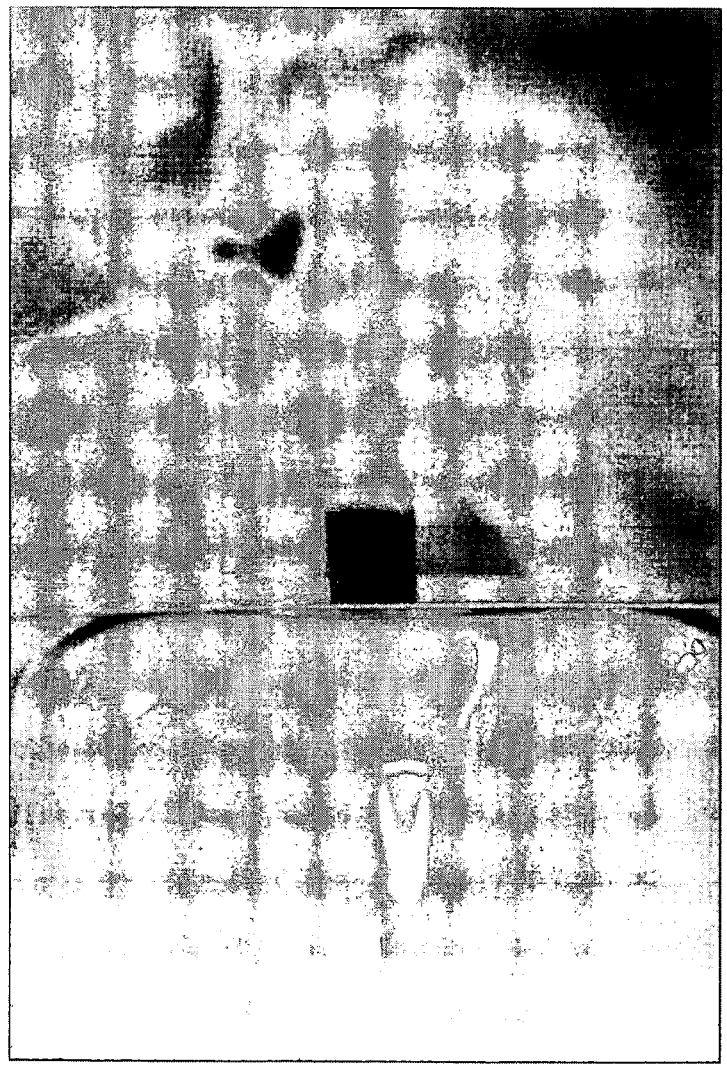
FIG. 38 is a photograph illustrating an osteochondral plug.

Continuing to block 2322 of FIG. 23, the osteochondral chisel and harvest guide can be removed from the condyle, as shown in FIG. 35. FIG. 36 depicts the condyle with the osteochondral chisel and harvest guide removed therefrom. Moreover, at block 2324 of FIG. 23, one or more osteochondral plugs can be removed from the condyle. In a particular embodiment, as shown in FIG. 37, the osteochondral plugs can be removed from the condyle using a band saw. Alternatively, the osteochondral plugs can be removed using another type of saw or sharp, bladed implement. FIG. 38 depicts a single osteochondral plug that can be harvested using the method described herein. At block 2326 of FIG. 23, one or more osteochondral plugs can be packaged for delivery to a user, e.g., a surgeon. The method can end at state 2328.

The osteochondral chisel assembly and the harvest guide assembly can also be used to create a recipient socket. The method to create a recipient socket can be similar to the method for harvesting an osteochondral plug. For example, the harvest guide can be affixed to the recipient bone in a similar fashion. Moreover, the osteochondral chisel can be driven through the harvest guide and into the recipient bone similar to the manner described herein. Using similar methods allows the geometry of the osteochondral plug to closely match the geometry of the recipient socket and surrounding tissue in which the recipient socket is created.

Description of a Trephine

Figure 39:
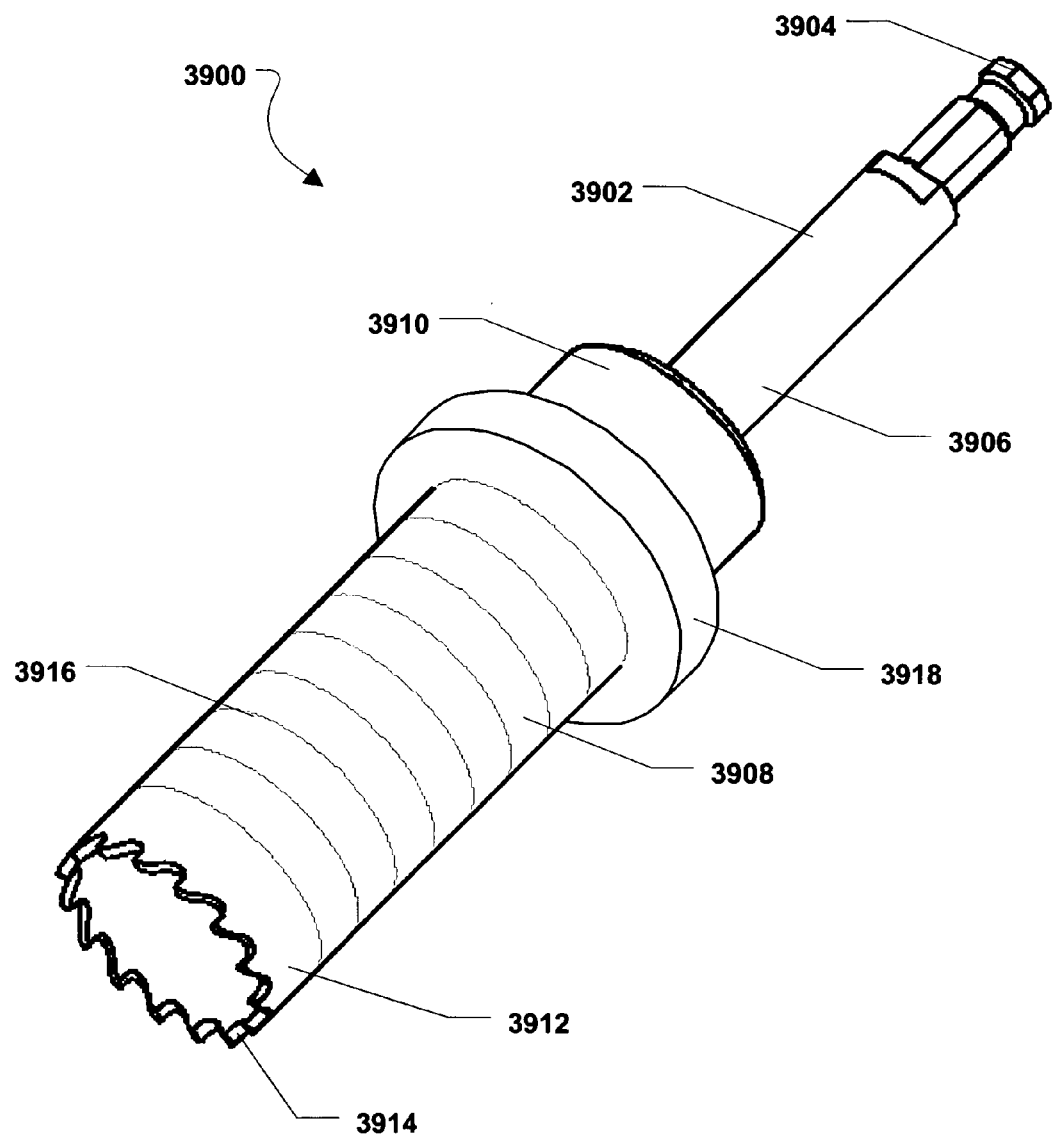
FIG. 39 is a perspective view of a trephine.
Figure 40:
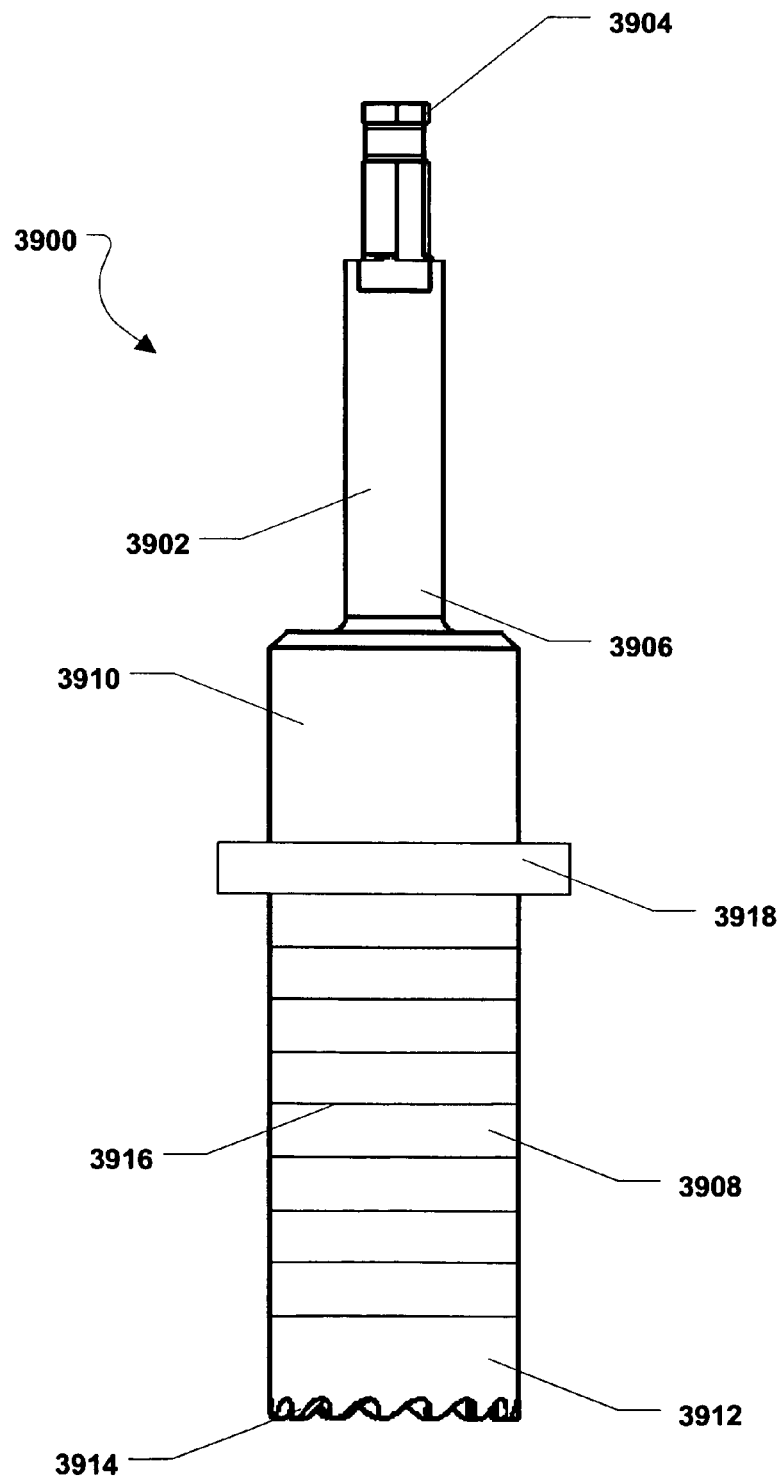
FIG. 40 is a plan view of the trephine.
Figure 41:
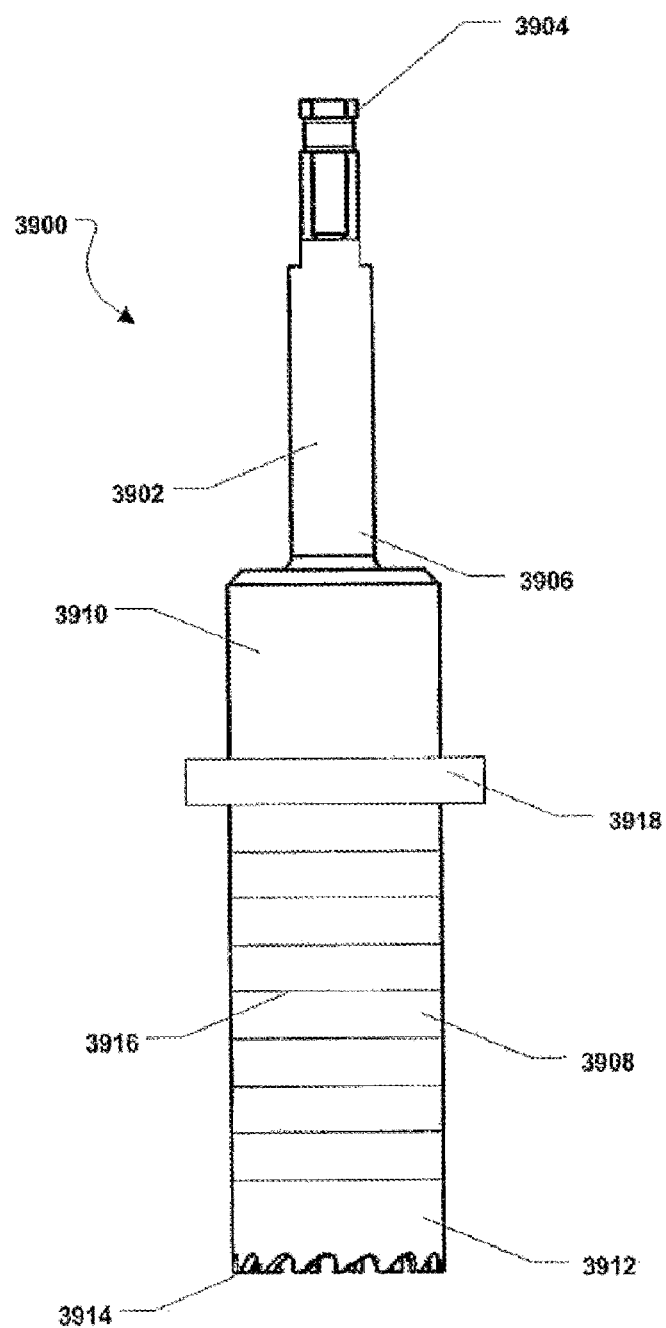
FIG. 41 is another plan view of the trephine.

Referring to FIG. 39 through FIG. 41, an embodiment of a trephine is shown and is generally designated 3900. As shown, the trephine 3900 can include a shaft 3902 having a proximal end 3904 and a distal end 3904. In a particular embodiment, the proximal end 3904 of the shaft 302 can be configured to be received within a drill chuck, e.g., a drill chuck of a surgical drill.

As indicated in FIG. 39 through FIG. 41, the trephine 3900 can include a hollow cutting head 3908 that can extend from the distal end 3904 of the shaft 3902. The cutting head 3908 of the trephine 3900 can include a proximal end 3910 and a distal end 3912. As shown, the proximal end 3910 of the cutting head 3908 can be attached to the distal end 3906 of the shaft 3902.

FIG. 39 through FIG. 41 further indicate that the distal end 3912 of the cutting head 3908 can be formed with a plurality of cutting teeth 3914. As the trephine 3900 is rotated, e.g., by a surgical drill, the cutting teeth 3914 can cut into tissue, e.g., bone. As further illustrated in FIG. 39 through FIG. 41, the cutting head 3908 of the trephine 3900 can include a plurality of depth indicators 3916. When used in conjunction with a harvest guide, described below, the depth indicators 3916 can indicate a penetration depth of the cutting head 3908. The depth indicators 3916 can be laser etched, or otherwise formed, at predetermined locations along the cutting head 3908 of the trephine 3900 between the distal end 3912 of the cutting head 3908 and the proximal end 3910 of the cutting head 3908.

Further, the cutting head 3908 can include a depth stop 3918 that can circumscribe the cutting head 3908. When the trephine 3900 is used in conjunction with a harvest guide, described below, the depth stop 3918 can prevent the cutting head 3908 of the trephine 3900 from moving too far through the harvest guide and penetrating too deeply into a patient.

Description of a Second Embodiment of a Harvest Guide Assembly

Figure 42:
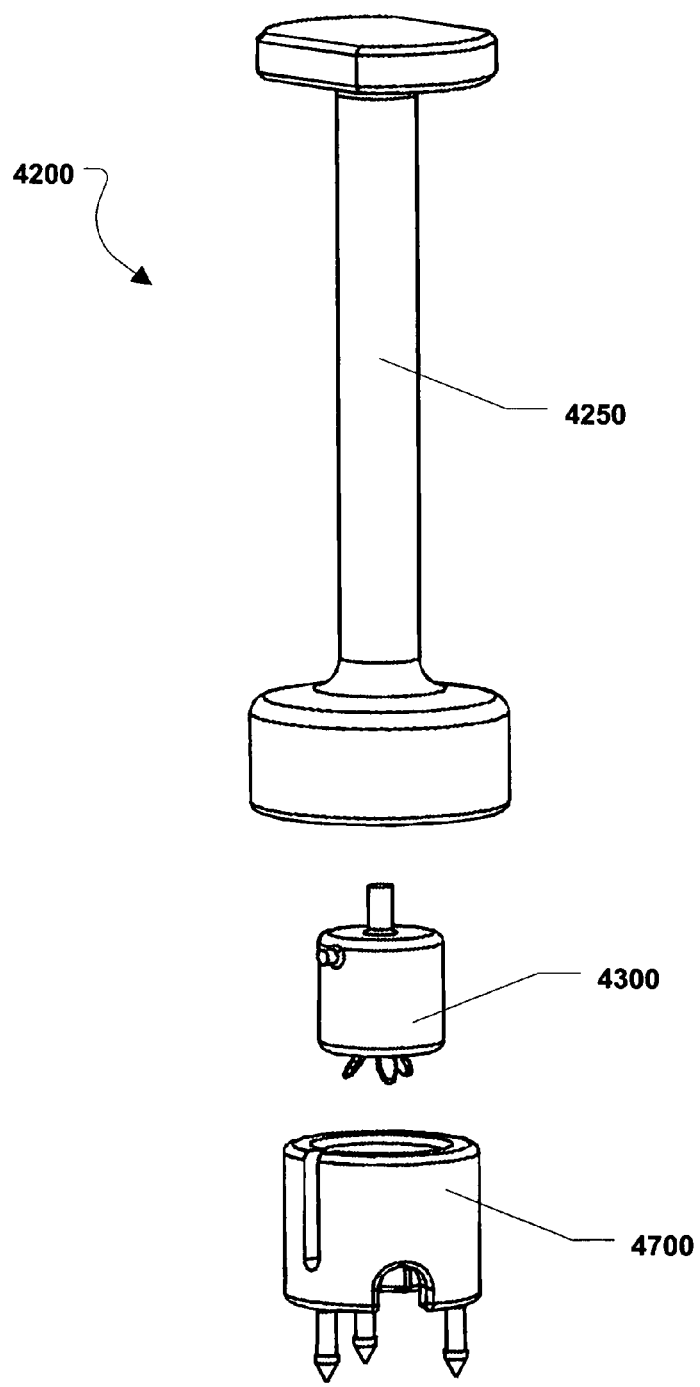
FIG. 42 is a plan view of a second embodiment of a harvest guide assembly.

Referring to FIG. 42, a second embodiment of a harvest guide assembly is shown and is generally designated 4200. As depicted in FIG. 42, the harvest guide assembly 4200 can include an impactor 4250, an orientation guide 4300, and a harvest guide 4700.

Description of an Impactor Associated with the Second Harvest Guide Assembly

In a particular embodiment, the impactor 4250 can be configured similar to the impactor described above in conjunction with FIG. 11 through FIG. 14. During use, the impactor 4250 can be placed around the harvest guide 4700. Moreover, a hammer can be used to strike the impactor 4250. The impactor 4250 can transmit the impact from the hammer to the harvest guide 4700 and the harvest guide 4700 can be driven into a condyle.

Description of an Orientation Guide Associated with the Second Harvest Guide Assembly Referring to FIG. 43 through FIG. 46, details concerning the orientation guide 4300 associated with the second harvest guide assembly 4200 (FIG. 42) can be seen. As depicted, the orientation guide 4300 can include a generally cylindrical body 4302. The body 4302 can include a top surface 4304 and a bottom surface 4306. A first post 4308 can extend substantially perpendicular from the top surface 4304 of the body 4302. Moreover, a second post 4310 can extend radially outward from the body 4302. The second post 4310 can be substantially perpendicular to the first post 4308.

Figure 43:
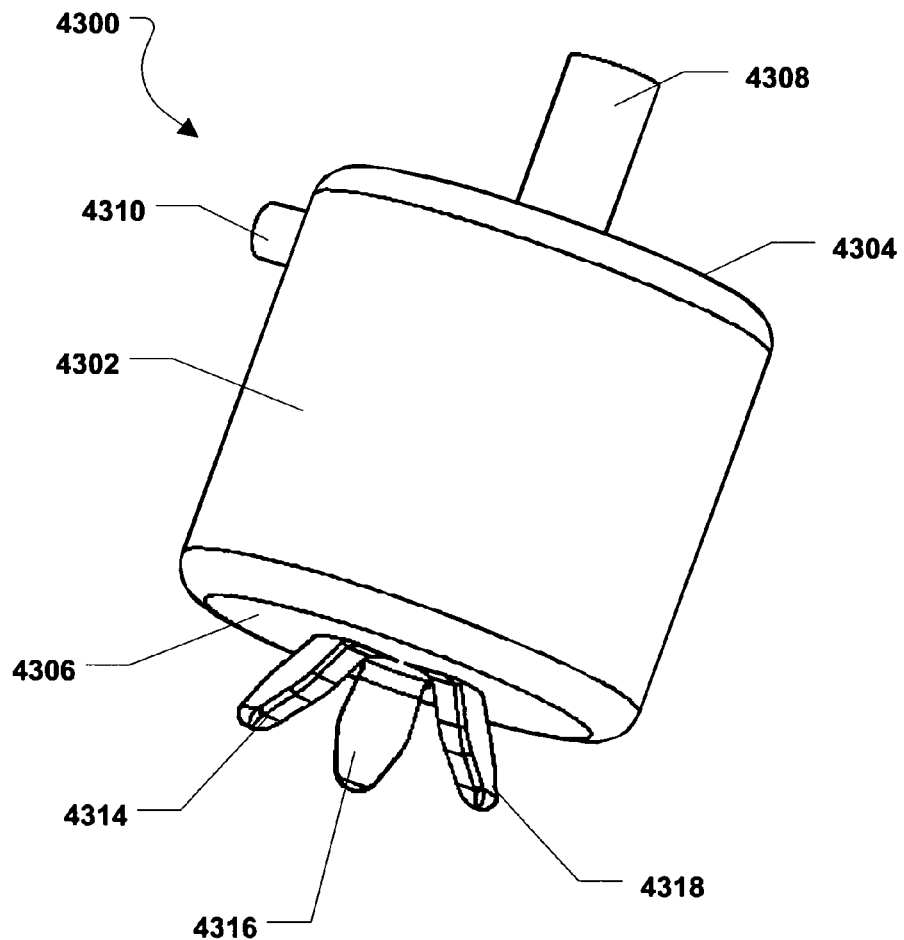
FIG. 43 is a perspective view of an orientation guide associated with the second harvest guide assembly.
Figure 44:
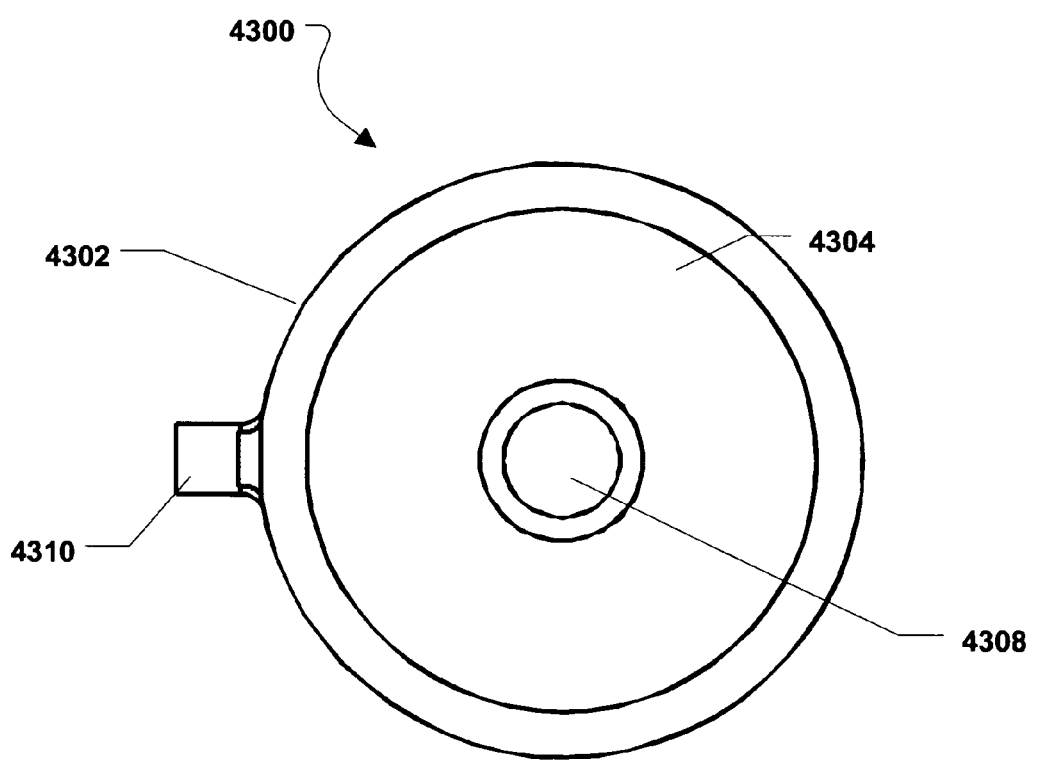
FIG. 44 is a top plan view of the orientation guide.
Figure 45:
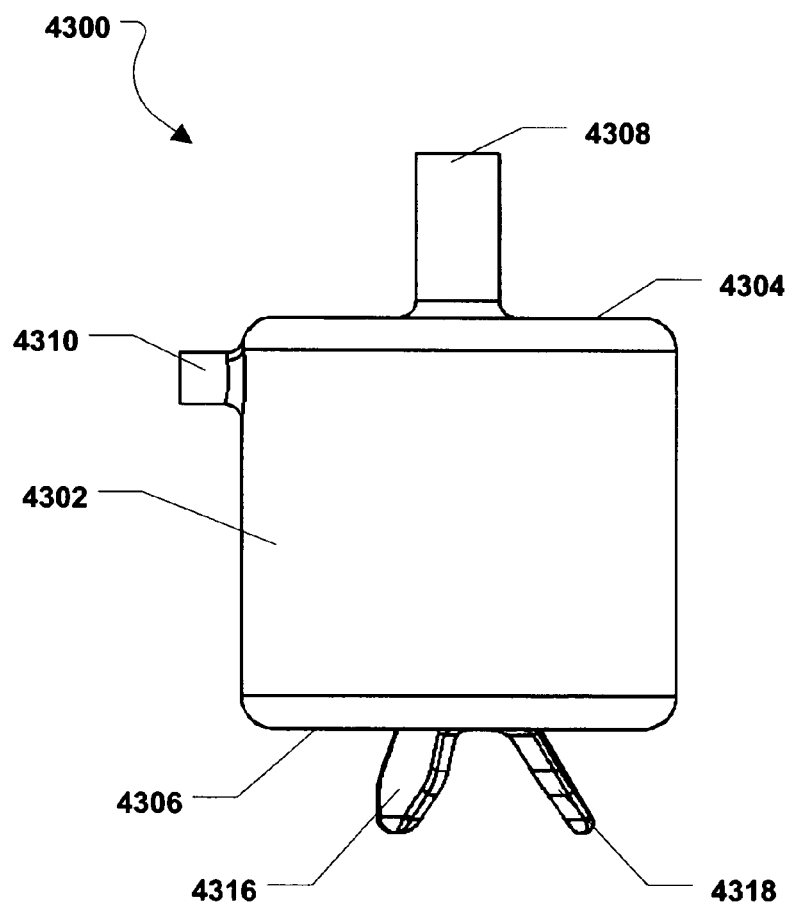
FIG. 45 is a first lateral plan view of the orientation guide.
Figure 46:
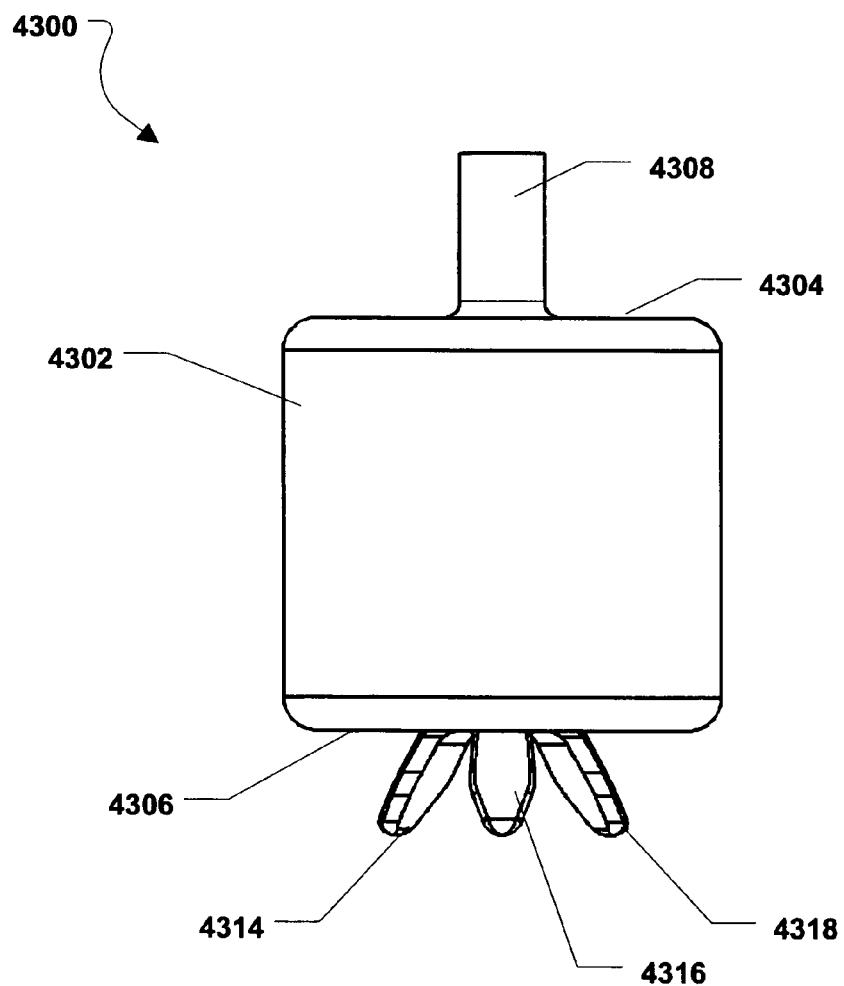
FIG. 46 is a second lateral plan view of the orientation guide.
Figure 47:
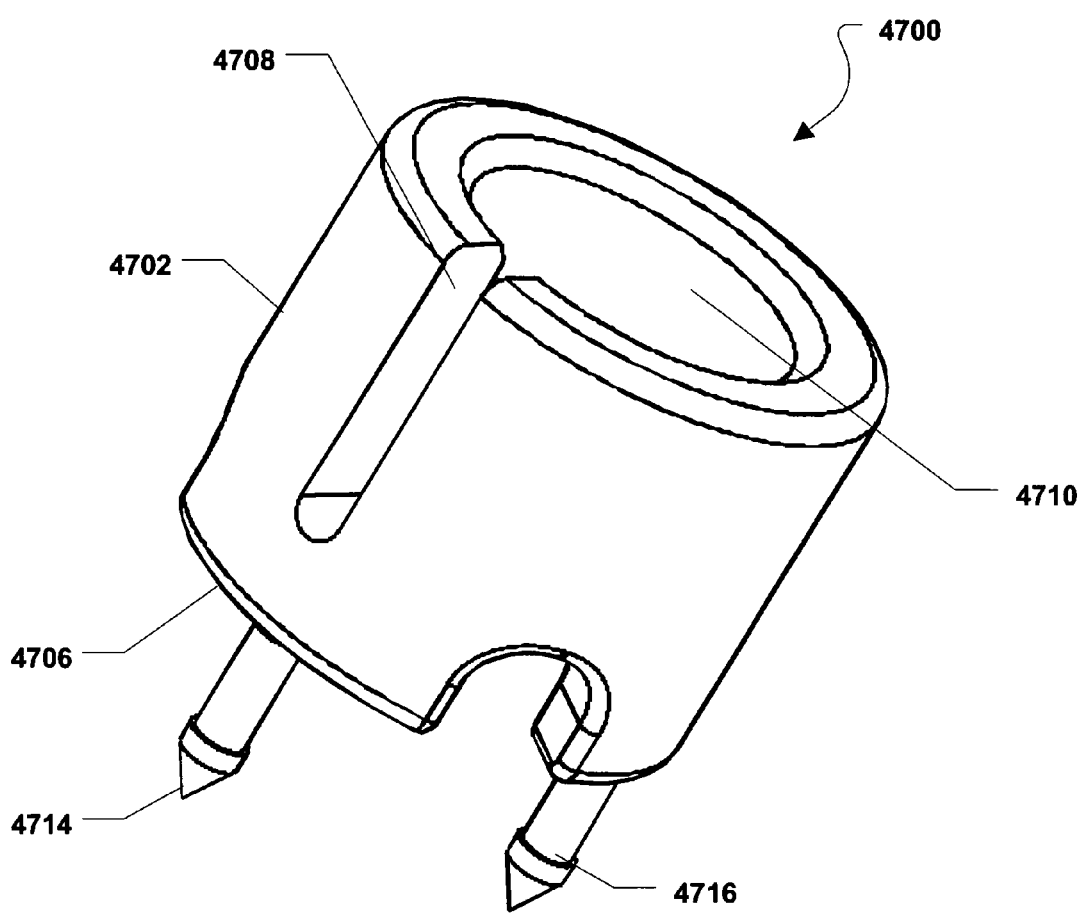
FIG. 47 is a perspective view of a harvest guide associated with the second harvest guide assembly.
Figure 48:
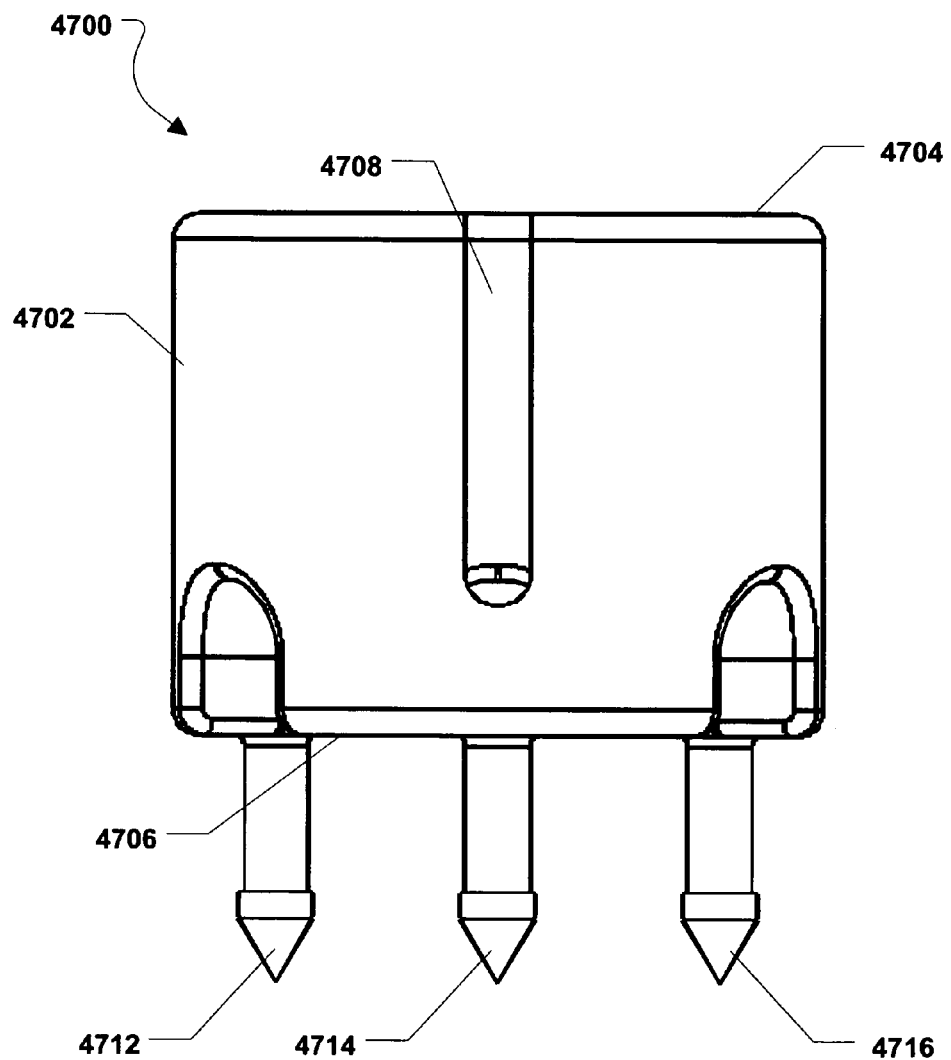
FIG. 48 is a first lateral plan view of the harvest guide.
Figure 49:
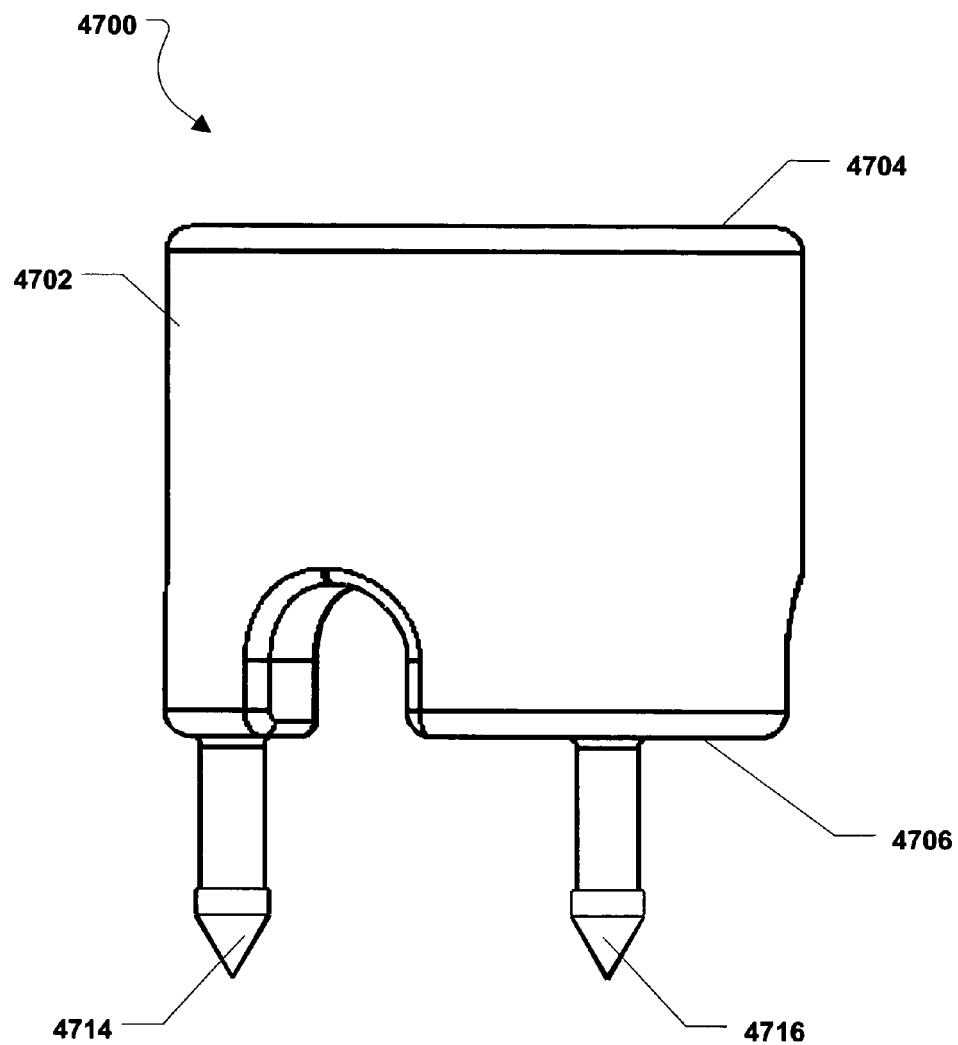
FIG. 49 is a second lateral plan view of the harvest guide.
Figure 50:
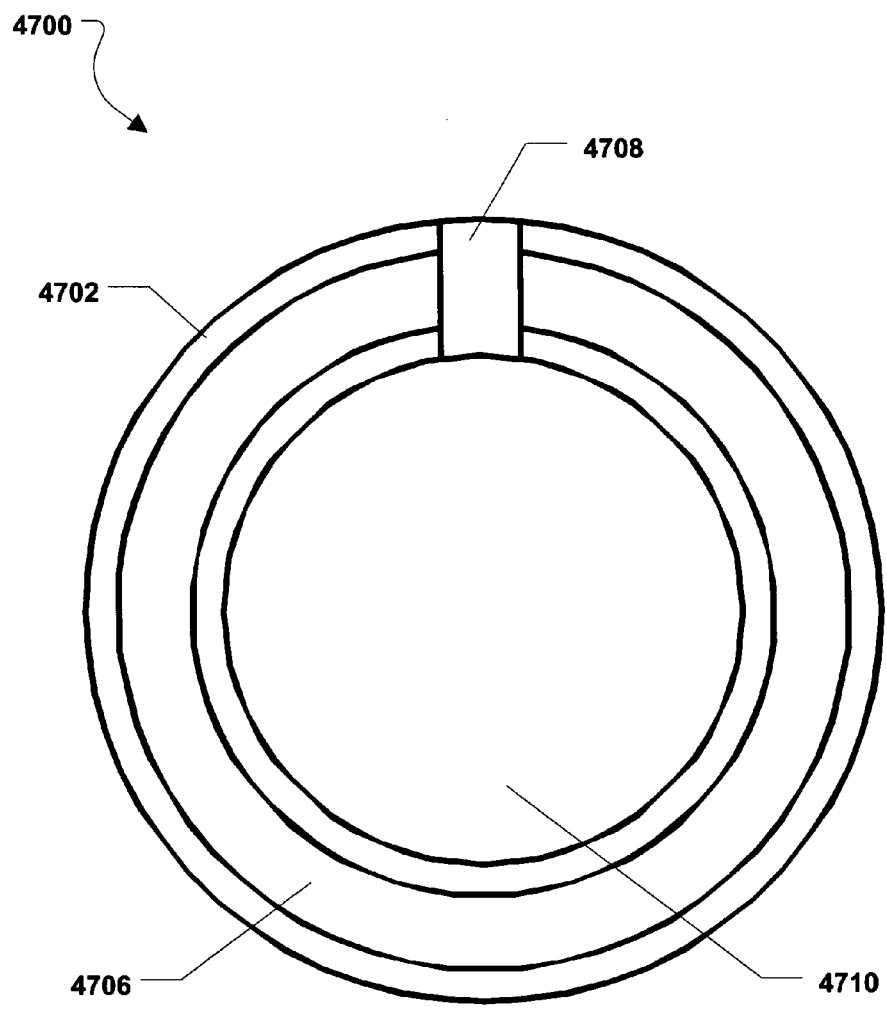
FIG. 50 is a top plan view of the harvest guide.

FIG. 43, FIG. 45, and FIG. 46 further indicate that the orientation guide 4300 can include a first foot 4314, a second foot 4316, and a third foot 4318 extending from the bottom surface 4306 of the body 4302. In a particular embodiment, each foot 4314, 4316, 4318 can extend from the bottom surface 4306 at an angle relative to the bottom surface 4306. Accordingly, in a particular embodiment, the orientation guide 4300 can be an orientation tripod having three feet on which the orientation tripod can rest.

During use, the orientation guide 4300 can be fitted into the harvest guide 4700 (FIG. 42). Further, the orientation guide 4300 and harvest guide 4700 (FIG. 42) can be placed on a rounded surface of a condyle. The orientation guide 4300, e.g., each foot 4314, 4316, 4318 thereof, can ensure proper placement and alignment of the harvest guide 4700 (FIG. 42) prior to the harvest guide 4700 (FIG. 42) being driven into the condyle, as described herein. After the harvest guide 4700 (FIG. 42) is driven into the condyle, the orientation guide 4300 can be removed from the harvest guide 4700 (FIG. 42).

When the orientation guide 4300 is placed within the harvest guide 4700 (FIG. 42), as described herein, the second post 4310 that extends from the body 4302 of the orientation guide 4300 can extend through a slot formed in the harvest guide 4700 (FIG. 42). The second post 4310 can facilitate placement and alignment of the orientation guide 4300 within the harvest guide 4700 (FIG. 42). Further, the first post 4308 can facilitate retrieval of the orientation guide 4300 from within the harvest guide 4700 (FIG. 42).

Description of a Harvest Guide Associated with the Second Harvest Guide Assembly Referring to FIG. 47 through FIG. 50, the details concerning the harvest guide 4700 associated with the second harvest guide assembly 4200 (FIG. 42) can be seen. As shown, the harvest guide 4700 can include a generally cylindrical body 4702. The body 4702 can include a top 4704 and a bottom 4706. Further, the body 4702 can include a slot 4708 and an interior cavity 4710 formed therein. The slot 4708 can extend from the top 4704 of the body 4702 partially along the length of the body 4702. The interior cavity 4710 can be sized and shaped to receive the orientation guide 1500, i.e., the interior cavity 4710 can be generally cylindrical.

FIG. 47 through FIG. 50 further indicate that the harvest guide 4700 can include a first tissue engagement post 4712, a second tissue engagement post 4714, and a third tissue engagement post 4716. The tissue engagement posts 4712, 4714, 4716 can extend from the bottom 4706 of the body 4702. Further, the tissue engagement posts 4712, 4714, 4716 can extend substantially perpendicularly from the bottom 4706 of the body 4702.

As described herein, the orientation guide 4300 (FIG. 43 through FIG. 46) can fit into the internal cavity 4710 formed in the body 4702 of the harvest guide 4700. Further, the second post 4310 (FIG. 43 through FIG. 45) that extends from the body 4302 (FIG. 43 through FIG. 45) of the orientation guide 4300 (FIG. 43 through FIG. 45) can extend through the slot 4708 formed in the body 4702 of the harvest guide 4700. Additionally, after the harvest guide 4700 is driven into a condyle, as described herein, the tissue engagement posts 4712, 4714, 4716 can engage the condyle and prevent the harvest guide 4700 from moving relative to the condyle. Further, after the orientation guide 4300 (FIG. 43 through FIG. 46) is retrieved from within the harvest guide 4700, as described herein, the trephine 3900 (FIG. 39 through FIG. 41) can be placed within the harvest guide 4700 and rotated into the condyle using a rotary device, e.g., a surgical drill. The trephine 3900 (FIG. 39 through FIG. 41) can be used to harvest an osteochondral plug and to create a recipient socket for an osteochondral plug.

Description of a Second Method of Harvesting Osteochondral Plugs

Figure 51:
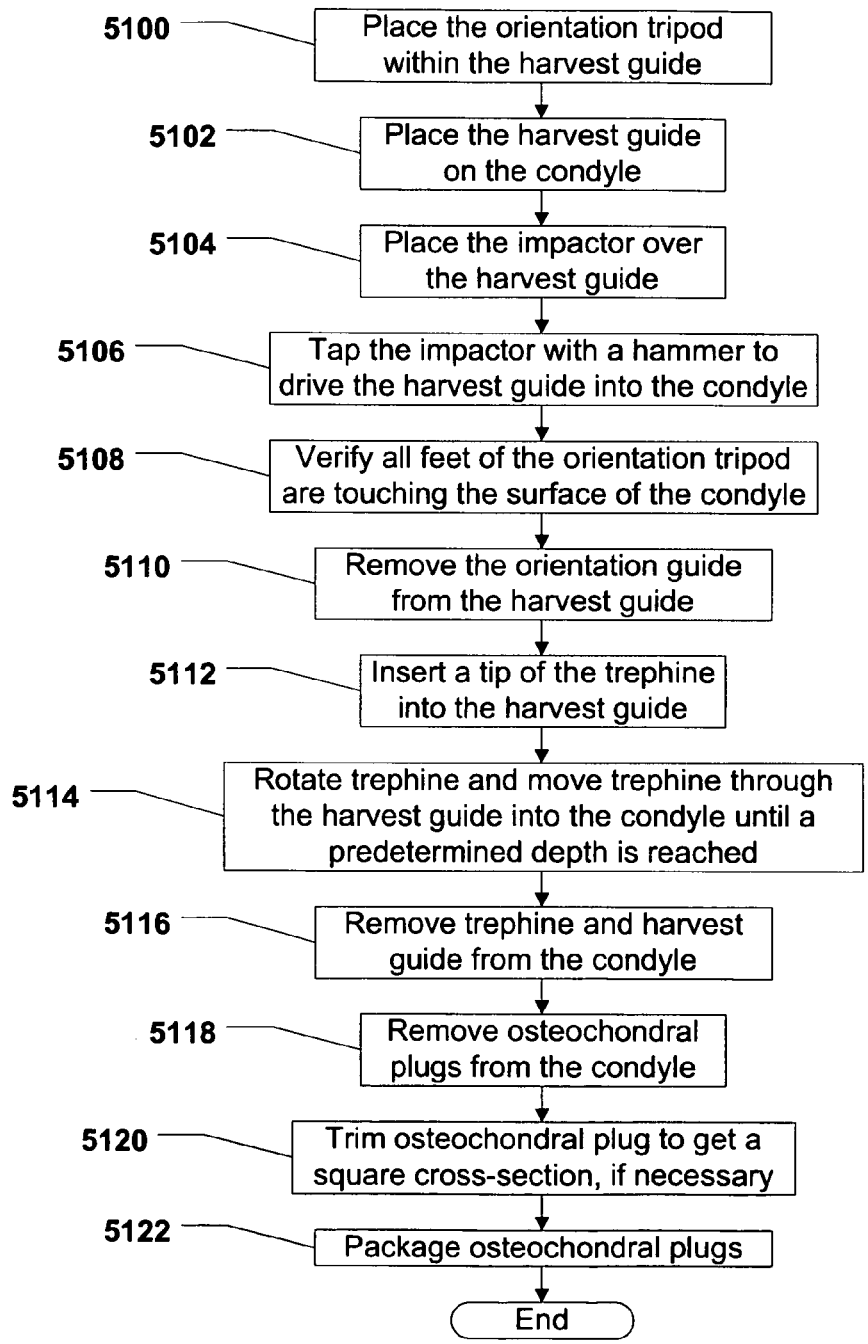
FIG. 51 is a flow chart illustrating a second embodiment of a method of harvesting an osteochondral plug.

FIG. 51 illustrates a flow chart of a second method of harvesting osteochondral plugs from bony tissue, e.g., from a condyle of a femur. In a particular embodiment, the osteochondral plugs can be harvested using a trephine and a harvest guide assembly according to one or more of the embodiments described herein. The harvest guide assembly can include an impactor, an orientation guide, and a harvest guide, described herein.

Commencing at block 5100 in FIG. 51, the orientation guide can be placed within the harvest guide. Moreover, at block 5102, the harvest guide and orientation guide assembly can be placed on a condyle. At block 5104, the impactor can be placed over the harvest guide. Further, at block 5106, the impactor can be tapped with a hammer in order to drive the harvest guide into the condyle.

Continuing to block 5108, a user, e.g., a surgeon, can verify that all of the feet extending from the orientation guide are touching the surface of the condyle. If one or more of the feet is not touching the surface of the condyle, the harvest guide can be removed and re-engaged with the surface of the condyle, as described above. On the other hand, if each of the feet is touching the surface of the condyle, the method can continue to block 5110 of FIG. 51 and the orientation guide can be removed from the harvest guide.

At block 5112 of FIG. 51, the tip of the trephine can be inserted into the harvest guide. The harvest guide, when properly placed, can maintain the osteochondral chisel substantially perpendicular to a tangent through a point on the bony tissue aligned with the osteochondral chisel. Particularly, the harvest guide can maintain the osteochondral chisel substantially perpendicular to a tangent through a point on the bony tissue that is aligned with a longitudinal axis of the osteochondral chisel. Thereafter, at block 5114, the trephine can be rotated and moved through the harvest guide into the condyle until a predetermined depth is reached. In a particular embodiment, the trephine can be moved through the harvest guide until the stop on the trephine impacts the harvest guide. Alternatively, the trephine can be moved through the harvest guide until a particular depth indicator is substantially aligned with an upper surface of the harvest guide. Further, in a particular embodiment, the trephine can be moved through the harvest guide using a surgical drill. The trephine can cut a perimeter surface of the osteochondral plug.

Continuing to block 5116, the trephine and harvest guide can be removed from the condyle. Moreover, at block 5118, one or more osteochondral plugs can be removed from the condyle. At block 5120, the one or more osteochondral plugs can be trimmed in order to get a square cross-section, if necessary. Moving to block 5122, one or more osteochondral plugs can be packaged for delivery to a user, e.g., a surgeon. The method can end at state 5124.

The trephine and the harvest guide assembly can also be used to create a recipient socket. The method to create a recipient socket can be similar to the method for harvesting an osteochondral plug. For example, the harvest guide can be affixed to the recipient bone in a similar fashion. Moreover, the trephine can be moved through the harvest guide and into the recipient bone similar to the manner described herein. Using similar methods allows the geometry of the osteochondral plug to closely match the geometry of the recipient socket and surrounding tissue in which the recipient socket is created.

CONCLUSION

With the configuration of structure described above, the system for harvesting osteochondral plugs provides one or more devices that can facilitate the harvesting of osteochondral plugs from one or more condyles. Further, the system can be used to create recipient sockets in a condyle, or other bone, for receiving an osteochondral plug. A harvest guide of the system can maintain a cutting device, e.g., an osteochondral chisel, a trephine, or a combination thereof, substantially perpendicular to a tangent through a point on the condyle that is aligned with the cutting device. As such, the osteochondral plug can have a surface with a curvature that is substantially uniform from side to side. Further, the harvest guide can act as a stop for the controlling the length of insertion of the osteochondral chisel, or trephine, into the condyle. Accordingly, the harvest guide can control the length of the harvested osteochondral plug.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An impactor assembly for harvesting osteochondral plugs, comprising: a shaft having a proximal end and a distal end; a harvest guide cap extending from the distal end of the shaft; and a harvest guide configured to fit within the harvest guide cap, the harvest guide having an axis, a top, a sidewall with a slot extending from the top and a bottom, an interior cavity having a cross-section that is generally square or generally round, the inner cavity configured to receive either an orientation guide or a cutting device for orienting and harvesting osteochondral plugs; and a plurality of tissue engagement posts equal in axial length, extending substantially perpendicularly from the bottom of the harvest guide and configured to be driven into a bony tissue of a condyle and prevent the harvest guide from moving relative to the bony tissue of the condyle; the orientation guide further comprising: a body having an axis, a top, a sidewall perimeter and a bottom; a first foot extending from the bottom of the body; a second foot extending from the bottom of the body; a third foot extending from the bottom of the body and the first, second and third feet are equal in axial length, wherein the orientation guide is configured to rest on bony tissue and wherein the first foot, the second foot and the third foot are configured such that the orientation guide is properly oriented when all three of the first foot, the second foot and the third foot are in simultaneous contact with the bony tissue; a handle extending from the body, wherein the handle includes a portion that extends laterally beyond the sidewall perimeter and is substantially perpendicular to the axis to facilitate placement of the orientation guide within a sidewall slot of the harvest guide and facilitate retrieval of the orientation guide from within the harvest guide; wherein the orientation guide is configured to fit within the harvest guide and orient the harvest guide relative to bony tissue.

2. The harvest guide of claim 1, wherein the cutting device comprises an osteochondral chisel, a trephine, or a combination thereof.

3. The assembly of claim 1, wherein the impactor further comprises an internal cavity formed in the harvest guide cap, wherein the internal cavity is sized and shaped to fit over the harvest guide.

4. The assembly of claim 3, wherein the impactor further comprises an impact plate extending from the proximal end of the shaft.

5. A method for harvesting osteochondral plugs, comprising: placing an orientation guide within a harvest guide; engaging the harvest guide with bony tissue, wherein the harvest guide comprises a body having a top and a bottom, an interior cavity formed within the body from the top to the bottom configured to receive either the orientation guide for orienting the harvest guide on the bony tissue without penetrating the bony tissue with the orientation guide, or a cutting device, and at least one tissue engagement post extending substantially perpendicularly from the bottom of the body to maintain the cutting device substantially perpendicular to a tangent through a point on the bony tissue aligned with the cutting device, wherein the tissue engagement post of the harvest guide is configured to be driven into the bony tissue and prevent the harvest guide from moving relative to the bony tissue; removing the orientation guide from the harvest guide; and placing the cutting device within the harvest guide, wherein the cutting device is configured to harvest osteochondral plugs; the orientation guide further comprising: a body having an axis, a top, a sidewall perimeter and a bottom; a first foot extending from the bottom of the body; a second foot extending from the bottom of the body; a third foot extending from the bottom of the body and the first, second and third feet are equal in axial length, wherein the orientation guide is configured to rest on bony tissue and wherein the first foot, the second foot and the third foot are configured such that the orientation guide is properly oriented when all three of the first foot, the second foot and the third foot are in simultaneous contact with the bony tissue; a handle extending from the body, wherein the handle includes a portion that extends laterally beyond the sidewall perimeter and is substantially perpendicular to the axis to facilitate placement of the orientation guide within a sidewall slot of the harvest guide and facilitate retrieval of the orientation guide from within the harvest guide; wherein the orientation guide is configured to fit within the harvest guide and orient the harvest guide relative to bony tissue.

6. The method of claim 5, further comprising moving the cutting device through the harvest guide into the bony tissue to cut a perimeter surface of the osteochondral plug.

7. The method of claim 6, further comprising removing the cutting device from the bony tissue and the harvest guide.

8. The method of claim 7, further comprising removing the harvest guide from the bony tissue.

9. The method of claim 8, further comprising removing the osteochondral plug from the bony tissue.

10. The method of claim 5, further comprising placing the harvest guide and orientation guide on the bony tissue.

11. The method of claim 10, wherein the orientation guide has a first foot, a second foot, and a third foot extending therefrom, the method further comprising verifying that each foot is touching a surface of the bony tissue.

12. The method of claim 11, further comprising placing an impactor over the harvest guide.

13. The method of claim 12, further comprising tapping the impactor with a hammer in order to drive the harvest guide into the bony tissue.

14. The method of claim 5, wherein the cutting device comprises an osteochondral chisel, a trephine, or a combination thereof.

* * * * *